US012226740B2

(12) United States Patent
Isaksson et al.

(10) Patent No.: US 12,226,740 B2
(45) Date of Patent: Feb. 18, 2025

(54) STABILIZED FILTRATION DEVICE

(71) Applicant: Aquammodate AB, Stora Höga (SE)

(72) Inventors: Simon Isaksson, Stora Höga (SE); Martin Andersson, Mölndal (SE)

(73) Assignee: Retein AB, Stora Höga (SE)

( * ) Notice: Subject to any disclaimer, the term of this patent is extended or adjusted under 35 U.S.C. 154(b) by 541 days.

(21) Appl. No.: 17/434,075

(22) PCT Filed: Feb. 26, 2020

(86) PCT No.: PCT/SE2020/050213
§ 371 (c)(1),
(2) Date: Aug. 26, 2021

(87) PCT Pub. No.: WO2020/176030
PCT Pub. Date: Sep. 3, 2020

(65) Prior Publication Data

US 2022/0152559 A1 May 19, 2022

(30) Foreign Application Priority Data

Feb. 27, 2019 (SE) .................................... 1950252-5

(51) Int. Cl.
*B01D 67/00* (2006.01)
*B01D 69/10* (2006.01)
(Continued)

(52) U.S. Cl.
CPC ....... *B01D 69/144* (2013.01); *B01D 67/0079* (2013.01); *B01D 67/0088* (2013.01); *B01D 69/106* (2022.08); *B01D 69/107* (2022.08); *B01D 71/027* (2013.01); *B01D 71/74* (2013.01); *C02F 1/44* (2013.01); *C07K 14/39* (2013.01)

(58) Field of Classification Search
CPC ..... B01D 69/144; B01D 71/027; B01D 71/74
See application file for complete search history.

(56) References Cited

U.S. PATENT DOCUMENTS 9,943,812 B2 4/2018 Jeon et al.
2011/0259815 A1 10/2011 Montemagno
(Continued)

FOREIGN PATENT DOCUMENTS

WO 2010040353 A2 4/2010
WO 2010091078 A2 8/2010
WO 2015144724 A1 10/2015

OTHER PUBLICATIONS

Besanger et al. "Ion Sensing and Inhibition Studies Using the Transmembrane Ion Channel Peptide Gramicidin A Entrapped in Sol-Gel-Derived Silica" Analytical Chemistry, 75(5):1094-1101 (2003).
(Continued)

*Primary Examiner* — Bradley R Spies
(74) *Attorney, Agent, or Firm* — Myers Bigel, P.A.

(57) ABSTRACT

A macromolecule membrane structure (2) comprises a membrane (3) with water-channeling integral membrane proteins (IMPS) (1) and is coated, on a first surface, with a silica layer (4). The silica layer (4) stabilizes the macromolecule membrane structure (2) and the water-channeling IMPS (1) while maintaining the water-channeling function of the water-channeling IMPs (1). As a consequence of this stabilization, the macromolecule membrane structure (2) may be used in a filtration device (5) for various filtration operations, including water purification.

20 Claims, 12 Drawing Sheets

(51) Int. Cl.

| | |
|---|---|
| ***B01D 69/14*** | (2006.01) |
| ***B01D 71/02*** | (2006.01) |
| ***B01D 71/74*** | (2006.01) |
| ***C02F 1/44*** | (2023.01) |
| ***C07K 14/39*** | (2006.01) |

(56) References Cited

U.S. PATENT DOCUMENTS

| | | | |
|---|---|---|---|
| 2011/0284456 | A1 | 11/2011 | Brozell |
| 2016/0367949 | A1 | 12/2016 | Jeon et al. |

OTHER PUBLICATIONS

International Search Report and the Written Opinion of the International Searching Authority corresponding to International Patent Application No. PCT/SE2020/050213 (12 pages) (mailed May 26, 2020).

Luo et al. "Photo-induced proton gradients and ATP biosynthesis produced by vesicles encapsulated in a silica matrix" Nature Materials, 4(3):220-224 (2005).

Ji et al. "Recent developments in nanofiltration membranes based on nanomaterials" Chinese Journal of Chemical Engineering, 25:1639-1652 (2017).

Keiderling, U. "The new 'BerSANS-PC' software for reduction and treatment of small angle neutron scattering data" Applied Physics A: Materials Science and Processing, 74:S1455-S1457 (2002).

Nyblom et al. "Exceptional overproduction of a functional human membrane protein" Protein Expression and Purification, 56:110-120 (2007).

STABILIZED FILTRATION DEVICE

TECHNICAL FIELD

The invention generally relates to macromolecule membrane structures and to filtration devices comprising such macromolecule membrane structures and the use thereof in, for instance, water filtration.

BACKGROUND

Access to clean water is defined as a human right by the United Nations. However, hundreds of millions of people do not have access to clean drinking water and are at immediate risk of exposure to toxic levels of polluting substances in their drinking water.

Water treatment includes drinking water purification and wastewater treatment, where both processes usually include several treatment steps in order to reach a desired level of purity. Filtration is commonly employed in these processes and is, for instance, employed to prevent undesired compounds in drinking water and to limit the extent of pollution exerted upon marine ecosystems by wastewater discharge.

Filters used in water treatment can be divided into two main categories: size exclusion filters and solution-diffusion filters. Size exclusion filters have a certain pore size and, hence, prevent substances that are larger than the pores from entering the filtrate, also referred to as permeate in the art. A limitation of these filters is that the pore size cannot be tuned into small enough diameters to stop, for example, sodium and chloride ions to pass through the filter, which is needed in drinking water production from sea water, i.e., desalination. Drinking water production from seawater is becoming increasingly popular due to decreasing amounts of available and sufficiently pure fresh water. Solution-diffusion filters are crucial in desalination, which is commonly conducted through reverse osmosis (RO). The selective layer in RO filters usually consists of a thin film composite (TFC) polymer membrane formed in an interfacial polymerization process. Water filtration through TFC membranes is based on a solution-diffusion mechanism, in which water is first molecularly dissolving into a polymer matrix at the side of high chemical potential, whereby it diffuses through the polymer down a chemical potential gradient to finally desorb on the side of low chemical potential. To overcome the osmotic pressure involved, pumps are used to drive the filtration process. The rate-limiting step is the diffusion through the polymer matrix, which can be improved at the expense of decreased selectivity. Solution-diffusion filters, hence, suffer from sub-optimal water diffusion rates and therefore need large amounts of energy to purify water.

Advances in protein engineering and nanotechnology have opened up possibilities of utilizing biomimicry to perform highly selective water treatment. The main driving force behind this approach is the potential to combine high selectivity with high flux, which is not possible using synthetic TFC membranes. The development of filters based on biomimicry has proven problematic due to the limited stability of biological components, such as aquaporins, outside their native environment. Different approaches have therefore been explored in order to produce biomimetic filters that are stable enough for real-world use. One approach explored in order to stabilize aquaporins is to deposit aquaporin-containing supported lipid bilayers (SLBs) or proteoliposomes on porous supports. The most popular approach to date judged from scientific output is based on aquaporin insertion into amphiphilic block-copolymer (BCP) bilayers. Aquaporins have also been stabilized using other organic molecules, such as bolaamphiphiles, and in two-step processes where amphiphilic peptides were used for initial aquaporin stabilization followed by subsequent polymeric stabilization.

U.S. Pat. No. 9,943,812 relates to a filtration structure for increased stability and durability, which includes a porous support where macromolecule membrane structures including membrane proteins are fixed to each other and to the supportive pore walls with linkers.

WO 2010/040353 relates to methods of producing membranes or thin fabrics to selectively transport and/or filter compounds between fluids. The document discloses natural or genetically engineered proteins incorporated into polymeric vesicles that are conjugated to a thread to form a vesicle-thread conjugate.

WO 2015/144724 discloses a filtration membrane, which comprises a porous support and, covalently bonded to a surface thereof, a layer comprising a plurality of vesicles having transmembrane proteins incorporated therein. The vesicles are formed from an amphiphilic block copolymer and the vesicles are covalently linked together to form a coherent mass.

WO 2010/091078 discloses a nanofabricated membrane including polymerized proteoliposomes. The nanofabricated membrane is a bio-nano fused selective membrane using protein-incorporated UV-crosslinkable liposomes with a chemical reactive biocompatible interstitial matrix.

Ji et al., Recent developments in nanofiltration membranes based on nanomaterials, *Chinese Journal of Chemical Engineering* 2017, 25: 1639-1652 is a review of studies on nanofiltration membranes including metal and metal oxide nanoparticles, carbon-based nanomaterials, metal-organic frameworks (MOFS), water channel proteins, and organic micro-nanoparticles.

Despite the above mentioned approaches, the commercial potential of nanoscale biomimetic water filtration is still little explored. The main reasons for the limited commercial implementation are manufacturing difficulties, in particular related to formation of macroscopic defects in the selective layer and the lack of stability needed for practical use with membrane designs incorporating aquaporins. Despite the efforts invested in the development of biomimetic water filters through a variety of creative approaches, this area of research has therefore not yet been able to deliver real-world performance that is on par with its predicted potential.

SUMMARY

It is a general objective to provide a macromolecule membrane structure with improved mechanical properties.

It is a particular objective to provide such a macromolecule membrane structure having sufficient stability to be used in filtration devices.

These and other objectives are met by embodiments as disclosed herein.

The present invention is defined in the independent claims. Further embodiments of the invention are defined in the dependent claims.

An aspect of the embodiments relates to a macromolecule membrane structure comprising a membrane comprising water-channeling integral membrane proteins and coated, on a first surface of the membrane, with a silica layer.

Another aspect of the embodiments relates to a filtration device comprising a porous support comprising a plurality of pores and macromolecule membrane structures according to above.

A further aspect of the embodiments relates to a method of preparing a water filtrate. The method comprises filtering an aqueous solution through a macromolecule membrane structure according to above or a filtration device according to above to obtain the water filtrate.

Yet another aspect of the embodiments relates to a method for concentrating a compound dissolved or dispersed in an aqueous solution. The method comprises filtering the aqueous solution through a macromolecule membrane structure according to above or a filtration device according to above to obtain a water filtrate lacking the compound and a retentate comprising the compound at a higher concentration than the aqueous solution.

An aspect of the embodiments relates to a process for preparation of a macromolecule membrane structure. The process comprises contacting a membrane comprising water-channeling integral membrane proteins with a silica precursor to form a silica layer coated on a first surface of the membrane.

Another aspect of the embodiments relates to a process for preparation of a filtration device. The process comprises depositing a membrane comprising water-channeling integral membrane proteins onto and/or into a porous support. The process also comprises contacting the membrane comprising water-channeling integral membrane proteins deposited onto and/or into the porous support with a silica precursor to form a silica layer coated on a first surface of the membrane.

The present invention provides a stabilization of macromolecule membrane structures, such as proteoliposomes, incorporating water-channeling integral membrane proteins to enable usage of these structures in filtration devices and for various filtration applications. The coating of the membranes with the water-channeling integral membrane proteins with a silica layer achieves the stabilization while still maintaining the water channeling function of the water-channeling integral proteins.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Generally, all terms used herein are to be interpreted according to their ordinary meaning in the relevant technical field, unless a different meaning is clearly given and/or is implied from the context in which it is used. All references to a/an/the element, apparatus, component, means, step, etc. are to be interpreted openly as referring to at least one instance of the element, apparatus, component, means, step, etc., unless explicitly stated otherwise. The steps of any methods disclosed herein do not have to be performed in the exact order disclosed, unless a step is explicitly described as following or preceding another step and/or where it is implicit that a step must follow or precede another step. Any feature of any of the embodiments disclosed herein may be applied to any other embodiment, wherever appropriate. Likewise, any advantage of any of the embodiments may apply to any other embodiments, and vice versa. Other objectives, features and advantages of the enclosed embodiments will be apparent from the following description.

The invention generally relates to macromolecule membrane structures and to filtration devices comprising such macromolecule membrane structures and the use thereof in, for instance, water filtration.

The present invention is based on the finding that the stability of macromolecule membrane structures incorporating integral membrane proteins (IMPs), such as such as transmembrane proteins (TPs), can be increased by coating a surface of the membrane with a silica layer. Such a surface coating with silica could furthermore be performed while maintaining the functionality of the IMPs or TPs, and preferably also the native conformation of the IMPs and TPs. Hence, silicification constitutes an efficient way of achieving sufficient stability in biomimetic membranes and filters to enable real-world implementation of such macromolecule membrane structures in practical applications in, for instance, filtration devices and water filtration.

The invention therefore relates to a macromolecule membrane structure comprising a membrane comprising water-channeling IMPs or TPs and coated, on a first surface of the membrane, with a silica layer.

Figure 1:
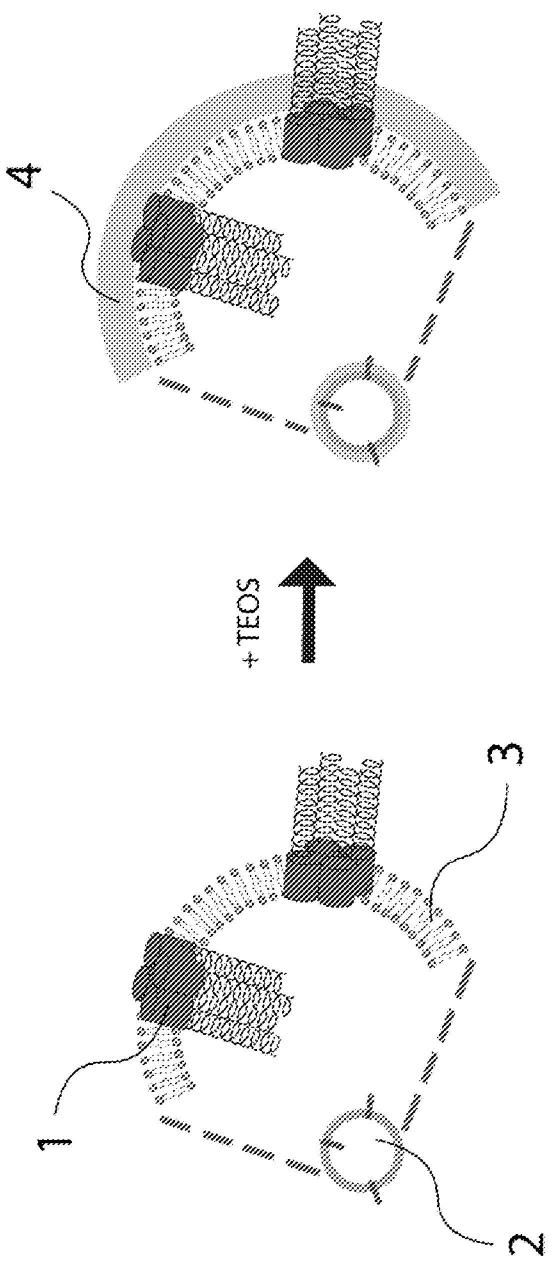
FIG. 1—Schematic drawings depicting proteoliposome silicification. After addition of tetraethyl orthosilicate (TEOS) a silica shell is deposited on the proteoliposome consisting of human aquaporin 4 (hAQP4) and 1-palmitoyl-2-oleoyl-sn-glycero-3-phosphocholine (POPC) lipids.

FIG. 1 schematically illustrates an example of such a macromolecule membrane structure in the form of a vesicle 2 of a lipid bilayer membrane 3 comprising water-channeling IMPs 1, also referred to as protein-containing liposome or proteoliposome 2 in the art with water-channeling IMPs 1. The proteoliposome 2 has, in this example, a silica layer or shell 4 on its outer surface.

The membrane 3 of the macromolecule membrane structure 2 is preferably a bilayer membrane 3, i.e., a double layer membrane 3 comprising two layers. The layers of the bilayer membrane 3 are preferably composed of amphiphilic molecules, i.e., molecules having a hydrophilic part and a lipophilic or hydrophobic part.

In a particular embodiment, the membrane 3 of the macromolecule membrane structure 2 is a lipid bilayer membrane 3. Hence, the amphiphilic molecules are amphiphilic lipids. Non-limiting, but illustrative, examples of such amphiphilic lipids include phosphatidylcholine, phosphatidylserine, phosphatidylethanolamine, phosphatidylglycerol, phosphatidylinositol, cardiolipin, cholesterol, sphingomyelin, asolectin, diphytanoylphosphatidylcholine (DPhPC), 1,2-dipalmitoyl-sn-glycero-3-phosphocholine (DPPC), 1,2-diheptanoyl-sn-glycero-3-phosphocholine (DHPC), 1,2-dihexanoyl-sn-glycero-3-phosphoethanolamine (DHPE), 1,2-dimyristoyl-sn-glycero-3-phosphocholine (DMPC), dimyristoyl phosphatidylserine (DMPS), dimyristoyl phosphatidylglycerol, dilauroyl phosphatidycholine (DLPC), 1,2-dimyristoyl-sn-glycero-3-phosphoethanolamine (DMPE), 1,2-dimyristoyl-sn-glycero-3-[phospho-rac-(1-glycerol)] (DMPG), lyso PC, such as 1-myristoyl-2-hydroxy-sn-glycero-3-phosphocholine (14:0 lyso PC) or 1-palmitoyl-2-hydroxy-sn-glycero-3-phosphocholine (16:0 lyso PC), lyso PE, such as 1-palmitoyl-2-hydroxy-sn-glycero-3-phosphoethanolamine (16:0 lyso PE) or 1-oleoyl-2-hydroxy-sn-glycero-3-phosphoethanolamine (18:1 lyso PE), 1,2-didecanoyl-sn-glycero-3-phosphocholine (DDPC), 1,2-dierucoyl-sn-glycero-3-phosphate (DEPA), 1,2-erucoyl-sn-glycero-3-phosphocholine (DEPC), 1,2-dierucoyi-sn-alycero-3-phosphoethanolamine (DEPE), 1,2-linoleoyl-sn-glycero-3-phosphocholine (DLOPC), 1,2-dilauroyl-sn-glycero-3-phosphate (DLPA), 1,2-dilauroyl-sn-glycerco-3-phosphoethanolamine (DLPE), 1,2-dilauroyl-sn-glycero-3-phosphoserine (DLPS), 1,2-dimyristoyl-sn-glycero-3-phosphate (DMPA), 1,2-dimyristoyl-sn-glycero-3-phosphoserine (DMPS), 1,2-dioleoyl-sn-glycero-3-phosphate (DOPA), 1,2-oleoyl-sn-glycero-3-phosphocholine (DOPC), 1,2-dioleoyl-sn-glycero-3-phosphoethanolamine (DOPE), 1,2-dioleoyl-sn-glycero-3-phosphoserine (DOPS), 1,2-dipalmitoyl-sn-glycero-3-phosphate (DPPA), 1,2-dipalmitoyl-sn-glycero-3-phosphoethanolamine (DPPE), 1,2-dipalmitoyl-sn-glycerco-3-phosphoserine (DPPS), 1,2-distearoyl-sn-glycero-3-phosphate (DSPA), 1,2-distearoyl-sn-glycero-3-phosphocholine (DSPC), 1,2-diostearpyl-sn-glycero-3-phosphoethanolamine (DSPE), 1-myristoyl-2-stearoyl-sn-glycero-3-phosphocholine (MSPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-oleoyl-sn-glycero-3-phosphoethanolamine (POPE), 1-palmitoyl-2-stearoyl-sn-glycero-3-phosphocholine (PSPC), 1-stearoyl-2-myristoyl-sn-glycero-3-phosphocholine (SMPC), 1-stearoyl-2-oleoyl-sn-glycero-3-phosphocholine (SOPC), 1-stearoyl-2-palmitoyl-sn-glycero-3-phosphocholine (SPPC), and a mixture thereof. A currently preferred example of amphiphilic lipid is POPC.

The amphiphilic lipid may also, or as an alternative, be selected from natural sources, such as a lipid from a cell membrane and/or from an organelle. Examples of such organelles include nucleus, mitochondria, chloroplasts, endoplasmic reticula, Golgi apparatus, lysosomes.

In fact, the membrane of the macromolecule membrane structure may indeed be an intact cell membrane, such as a yeast cell or a bacterial cell, which comprises water-channeling IMPs and are coated with a silica layer. Furthermore, organelles comprising such water-channeling IMPs could be coated with a silica layer to form a macromolecule membrane structure according to the invention. In these cases, the cell or organelle membrane typically comprise other membrane proteins than the water-channeling IMPs.

The membrane 3 may alternatively, or in addition, comprise cross-linkable lipids, i.e., amphiphilic lipids having cross-linkable chemical structures in the hydrophobic part and/or in the hydrophilic part of the amphiphilic lipid molecule. Examples of such cross-linkable lipids are disclosed in WO 2010/091078 and include, among others, 1-palmitoyl-2-(10Z,12Z-tricosdiynoyl)-sn-glycero-3-phosphocholine, 1-palmitoyl-2-(10Z,12Z-tricosdiynoyl)-sn-glycero-3-phosphoethanolamine, 1,2-di-(10Z,12Z-tricosdiynoyl)-sn-glycero-3-phosphocholine and 1-2-(10Z, 12Z-tricosdiynoyl)-sn-glycero-3-phosphoethanolamine). The cross-linkable lipids are preferably UV-cross-linkable, i.e., crosslinking is induced by UV exposure.

The membrane could comprise a single type or species of amphiphilic lipids or a mixture of multiple, i.e., at least two, different types or species of amphiphilic lipids.

Alternatively, or in addition, the amphiphilic molecules of the membrane 3 could be amphiphilic copolymers, such as amphiphilic AB, ABA and/or ABC block copolymers. Illustrative, but non-limiting, examples of such amphiphilic copolymers include poly(methyloxazoline)-poly(dimethylsiloxane)-poly(methyloxazoline) (PMOXA-PDMS-PMOXA), poly(2-ethyl-2-oxazoline)-b-poly(dimethylsiloxane)-b-poly(2-ethyl-2-oxazoline) (PEtOz-PDMS-PEtOz), and a mixture thereof. More generally, the amphiphilic copolymer may comprise at least one hydrophilic block comprising (poly)2-$C_{1-3}$alkyl-2-oxazoline and at least one hydrophobic block comprising PDMS, such as ((poly)2-$C_{1-3}$alkyl-2-oxazoline)$_a$-PDMS$_b$-((poly)2-$C_{1-3}$alkyl-2-oxazoline)$_a$, wherein each a is independently a number between 5 and 100 and b is a number between 5 and 140. In the case of a membrane 3 with amphiphilic copolymers, the macromolecule membrane structure 2 is a proteopolymersome.

The macromolecule membrane structure 2 is preferably in the form of a vesicle, proteoliposome or proteopolymersome 2 as shown in FIG. 1. In such a case, the membrane 3 is a proteoliposome or proteopolymersome 2 and the outer surface of the proteoliposome or proteopolymersome 2 is coated with the silica layer 4.

In another embodiment, the macromolecule membrane structure 2 is a substantially flat or 2D membrane structure with the membrane 3 as a substantially flat or planar structure. The silica layer 4 is then applied to one of the surfaces of the flat or planar membrane 3.

In an embodiment, the water-channel IMPs 1 incorporated into the membrane 3 of the macromolecule membrane structure 2 are aquaporins 1.

Aquaporins, also called water channels, are IMPs from a larger family of major intrinsic proteins that form pores in the membrane of biological cells, mainly facilitating transport of water between cells. The cell membranes of a variety of different bacteria, fungi, animal and plant cells contain aquaporins, through which water can flow more rapidly into and out of the cell than by diffusing through the phospholipid bilayer. Aquaporin has six membrane-spanning alpha helical domains with both carboxylic and amino terminals on the cytoplasmic side. Two hydrophobic loops contain conserved asparagine-proline-alanine NPA motif.

In an embodiment, the aquaporins are selected from the group consisting of a human aquaporin (hAQP), a bovine aquaporin (bAQP), a fish aquaporin, a yeast aquaporin, a plant aquaporin and a bacterial aquaporin, and a mixture thereof.

There are 13 human aquaporins, which are divided into three subgroups; water selective (orthodox) aquaporins that solely transport water (hAQPO, hAQP1, hAQP2, hAPQ4, hAPQ5, hAQP6, hAQP8), aquaglyceroporins that, in addition to water, transport small uncharged solutes, such as glycerol, (hAQP3, hAQP7, hAQP9, hAQP10), and super-aquaporins (hAQP11, hAQP12), whose transport characteristics are to be further elucidated. In an embodiment, the hAQP is selected from the group consisting of hAQPO, hAQP1, hAQP2, hAQP3, hAQP4, hAQP5, hAQP6, hAQP7, hAQP8, hAQP9, hAQP10, hAQP11 and hAQP12, preferably selected from the group consisting of hAQPO, hAQP1, hAQP2, hAQP4, hAQP5, hAQP6, and hAQP8, i.e., the water selective human aquaporins, and is more preferably hAPQ4.

The bovine aquaporin is preferably bAQP1 and the fish aquaporin is preferably cpAQP1aa. A preferred example of a yeast aquaporin is Aqyl and a suitable bacterial aquaporin is AqpZ. Illustrative examples of plant aquaporins that can be used include SoPIP2; 1, AtTIP2; 1 and AtPIP2; 4.

In an embodiment, the membrane 3 comprises a single type or species of aquaporins 1. In another embodiment, the membrane 3 comprises multiple types or species of aquaporins 1.

In an embodiment, the silica layer 4 has an average thickness selected within a range of from 0.1 to 1000 nm, preferably from 1 to 100 nm, and more preferably from 1 to 10 nm. In a particular embodiment, the silica layer has an average thickness within a range of from 2 to 6 nm, preferably from 3 to 5 nm, and more preferably from 3 to 4 nm.

As previously mentioned herein, membranes 3 comprising water-channeling IMPs 1 can be coated with a silica layer 4 as disclosed herein while maintaining the water-channeling function of the water-channeling IMPs 1. Hence, the water-channel IMPs 1 are still functional in the macromolecule membrane structure 2 in terms of being capable of transporting water across the membrane 3 in the presence of the silica layer 4. In a particular embodiment, the silica layer 4 therefore does not prevent or block the water channeling or transporting function of the water-channeling IMPs 1.

In an embodiment, the silica layer 4 is a functionalized silica layer 4. Hence, the silica layer 4 comprises functionalized molecules that can exert a desired function to the macromolecule membrane structure 2. An example of such a function is a linking function. Hence, the functionalized molecules in the silica layer 4 can then be used to immobilize, attach or link, such as covalently link, the macromolecule membrane structure 2 to a support.

In a particular embodiment, the functionalized silica layer 4 comprises a silane, such as fluoroalkylsilane (FAS), an alkoxysilane, such as hexamethyldisilazane (HMDZ), or a combination thereof. These functionalized molecules can then be used to covalently link the macromolecule membrane structure 2 to a support using silane chemistry. For instance, FAS can be used to form covalent linkages between the silica layer and an alumina support, or a support having an alumina coating.

A macromolecule membrane structure 2 can be prepared in a process that comprises contacting a membrane 3 comprising water-channeling IMPs 1 with a silica precursor to form a silica layer 4 coated on a first surface of the membrane 3.

In an embodiment, the silica precursor is selected from the group consisting of a silicon alkoxide, a silane, a silicate, a silanol, a silazane, N-sec-butyl(trimethylsilyl)amine, and a combination thereof.

In an embodiment, the silicon alkoxide is selected from the group consisting of tetramethyl orthosilicate (TMOS), tetraethyl orthosilicate (TEOS), tetrapropyl orthosilicate, tetrabutylorthosilicate, methyltriethoxysiloxane (MTES), dimethyldiethoxysiloxane (DMDES), tetrakis(glycerol)orthosilicate (TGS), tetrakis-(2-hydroxyethyl)-orthosilicate (THEOS), and a combination thereof, In an embodiment, the silane is selected from the group consisting of allyltrimethoxysilane, (3-aminopropyl)triethoxysilane, bytyltrichlorosilane, chloropentamethyldisilane, 1,2-dichlorotetramethyldisilane, diethoxydiphenylsilane, [3-(diethylamino)propyl]trimethoxysilane, dimethoxydimethylsilane, dimethoxy(methyl)octylsilane, (3-glycidyloxypropyl)trimethoxysilane, hexamethyldisilane, isobutyl(trimethoxy)silane, methyltrichlorosilane, pentamethyldisilane, n-propyltriethoxysilane, tetraethylsilane, 1,1,2,2-tetramethyldisilane, tetramethylsilane, triethoxymethylsilane, triethoxyoctylsilane, trimethoxyphenylsilane, triethoxyphenylsilane, triethoxyvinylsilane, trimethoxymethylsilane, γ-aminopropyltriethoxysilane, silicon tetrachloride (tetrachlorosilane), silicon tetrabromide (tetrabromidesilane), γ-aminopropylsilanetriol (APSTOL), and a combination thereof.

In an embodiment, the silicate is sodium silicate (waterglass).

In an embodiment, the silanol is selected from the group consisting of tris(tert-pentoxy)silanol, tris(tert-butoxy)silanol, and a combination thereof.

In an embodiment, the silica precursor is TEOS.

In an embodiment, the membrane 3 is contacted with the silica precursor in a buffer solution comprising a buffering agent. Non-limiting, but illustrative, examples of buffering agents that can be used in the buffer solution include tris(hydroxymethyl)aminomethane (Tris), phosphate buffered saline (PBS), 4-(2-hydroxyethyl)-1-piperazineethanesulfonic acid (HEPES), 2-[[1,3-dihydroxy-2-(hydroxymethyl)propan-2-yl]amino]ethanesulfonic acid (TES), 2-(N-morpholino)ethanesulfonic acid (MES), and 3-(N-morpholino)propanesulfonic acid (MOPS). An example of a suitable buffering agent is Tris. The buffer solution may then be an aqueous Tris-HCl solution.

In an embodiment, the buffer solution comprises a salt to adjust or set the ionic strength of the buffer solution. Non-limiting, but illustrative, examples of salts that can be used include a chloride salt, a sulfate salt, a carbonate salt and a mixture thereof. Chloride salts that can be used according to the embodiments include NaCl, KCl, $CaCl_2$ and $MgCl_2$. $MgSO_4$ and $CaSO_4$ are suitable examples of sulfate salts, whereas $Na_2CO_3$ is a preferred example of a carbonate salt.

The pH of the buffer solution is at least partly determined based on the buffering agent or agents. The pH of the buffer solution could be an acidic pH, i.e., below 7, a neutral pH, i.e., around 7, or a basic pH, i.e., above 7. The pH of the buffer solution affects the characteristics of the formed silica layer 4. For instance, an acidic pH, such as pH 2, produces a more dense silica layer 4 as compared to a neutral or basic buffer solution. Correspondingly, silica layer formation in slightly basic conditions (pH 8) proceeded by an initial arrangement of silicic acid around the 3 followed by densification.

The water-channeling IMPs 1 in the 3 having selectivity for water effectively excluded specific reagents used in the silicification process from entering or passing through the membrane comprising the water-channeling IMPs 1. This was a significant and highly unexpected advantage of the invention since the reagents may otherwise negatively affect the 3 and the macromolecule membrane structure 2 and may contaminate a filtrate passing through the 3.

The macromolecule membrane structure 2 of the embodiments, such as prepared according to the above mentioned process, may contain a thin layer of water in between the 3 and the silica layer 4. Such a water layer may be enclosed during the preparation process and typically has a thickness in the nm or sub-nm range.

In an embodiment of the process for producing silica coated proteoliposomes 2 containing aquaporin 1, phosphatidylcholine lipids, such as 1-palmitoyl-2-oleoyl-sn-glycero-phosphatidylcholine (POPC), are first homogeneously dispersed in an aqueous buffer solution, which may, for example, contain either Tris or PBS to set the pH, and a salt, such as NaCl, to set the ionic strength. Lipids may or may not have been dissolved in a less polar solvent than water, such as chloroform ($CHCl_3$), followed by $CHCl_3$ removal prior to dispersion in the aqueous buffer solution. A mild detergent, such as n-octyl-β-D-glucoside (β-OG) or n-nonyl-β-D-glucoside (β-NG) may be added to solubilize the liposomes. Purified aquaporin stabilized in a mild detergent, such as β-OG or β-NG, is added to the liposome mixture. Detergent is then preferably removed from the mixture using, for example, polystyrene bead adsorption followed by subsequent removal, or dialysis using, for example, a cellulose acetate dialysis membrane having a molecular cut-off of 1000 Da or 2000 Da. This procedure results in multilamellar and polydisperse vesicles 2 containing aquaporin 1.

The vesicles 2 may, in an embodiment, be further processed prior to silicification in order to decrease the degree of multilamellarity and polydispersity. For instance, the vesicles 2 containing aquaporin 1 may be extruded through pores in, for example, polycarbonate extrusion membranes or nylon centrifugal filters having diameters in the range of from 30 nm to 1000 nm to decrease the degree of multilamellarity and polydispersity.

A layer 4 of silica in the thickness range of from 0.1 nm to 1000 nm may then be formed on the vesicles containing aquaporin 1. In an exemplary silica coating procedure, silicon alkoxide, such as TEOS, or cation-exchanged sodium silicate (water glass) is added to the vesicles 2 containing aquaporin 1. The silicon alkoxide may either be pre-hydrolyzed in a solution without vesicles 2 prior to addition to the vesicles 2 containing aquaporin 1 or added directly to the vesicles 2 containing aquaporin 1. Silicon alkoxide hydrolysis results in the formation of orthosilicic acid and Q1, Q2, and Q3 species of silicon alkoxide where 0, 1, 2, and 3 alkoxide groups are covalently attached to silicon due to incomplete hydrolysis of the silicon alkoxide. Condensation of these species in the presence of the vesicles 2 containing aquaporin 1 results in the formation of a layer 4 of silica on the outside of the vesicle 2 containing aquaporin 1. Silica-coated vesicles 2 containing aquaporins 1 may aggregate during condensation, which may lead to the formation of a second silica coating in the thickness range of from 0.1 nm to 300 nm on the aggregates.

In an embodiment, surface modification to the vesicles 2 containing aquaporin 1 may be performed subsequent to formation of the silica layer 4. In an exemplary procedure, a functional group, for example a silane, is introduced into the silica layer 4 of the vesicles 2 containing aquaporins 1. In an exemplary procedure, the coated vesicles 2 containing aquaporin 1 are placed in 1% (v/v) hexamethyldisilazane (HMDZ) in hexane. Accessible silanol groups (Si—OH) on the silica surface are partly substituted for methylated groups. Other examples of silanes that may be used include, but are not limited to, fluoroalkylsilanes (FAS) and alkoxysilanes.

Figure 7:
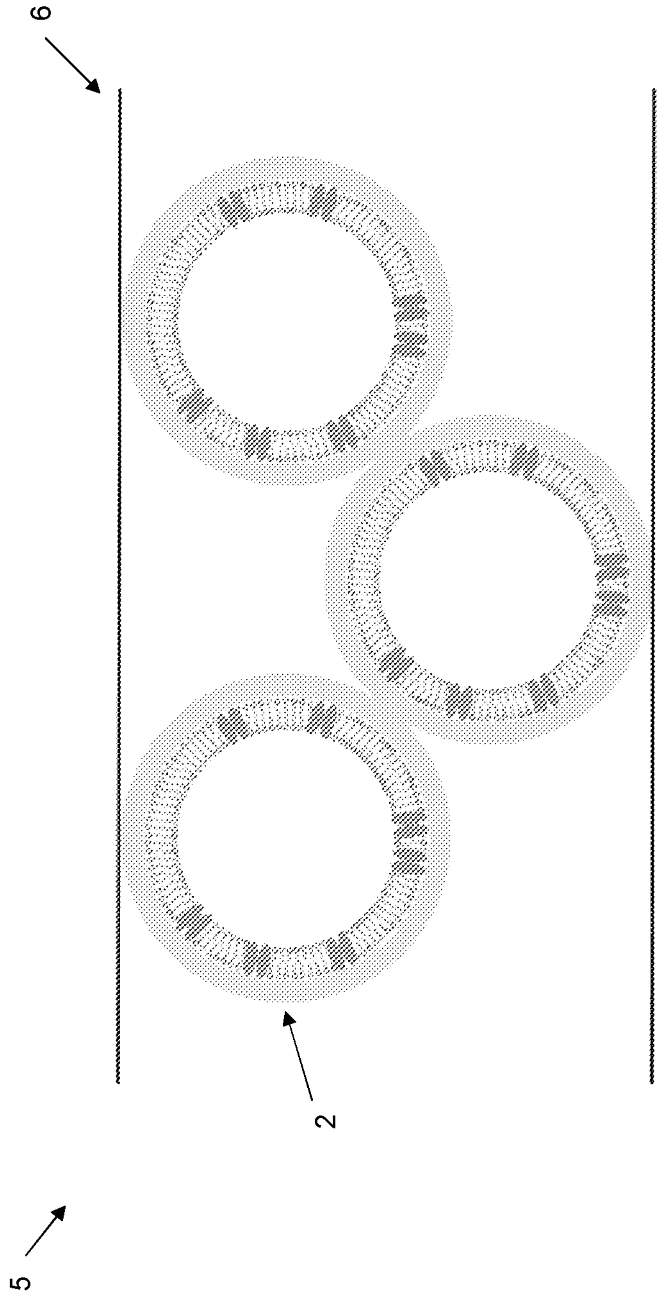
FIG. 7—Schematic illustration of a filtration device according to an embodiment.
Figure 8:
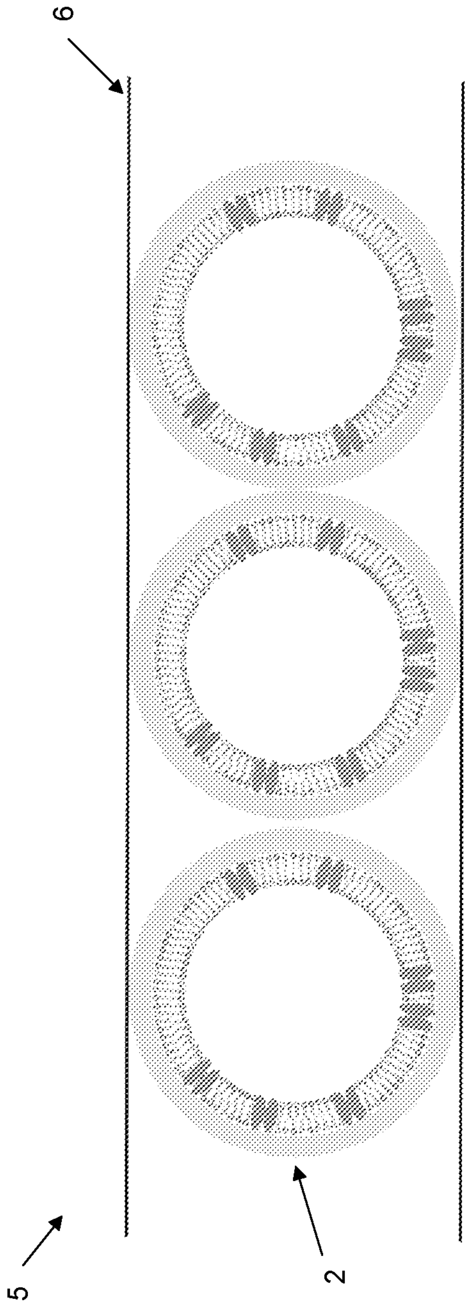
FIG. 8—Schematic illustration of a filtration device according to another embodiment.
Figure 9:
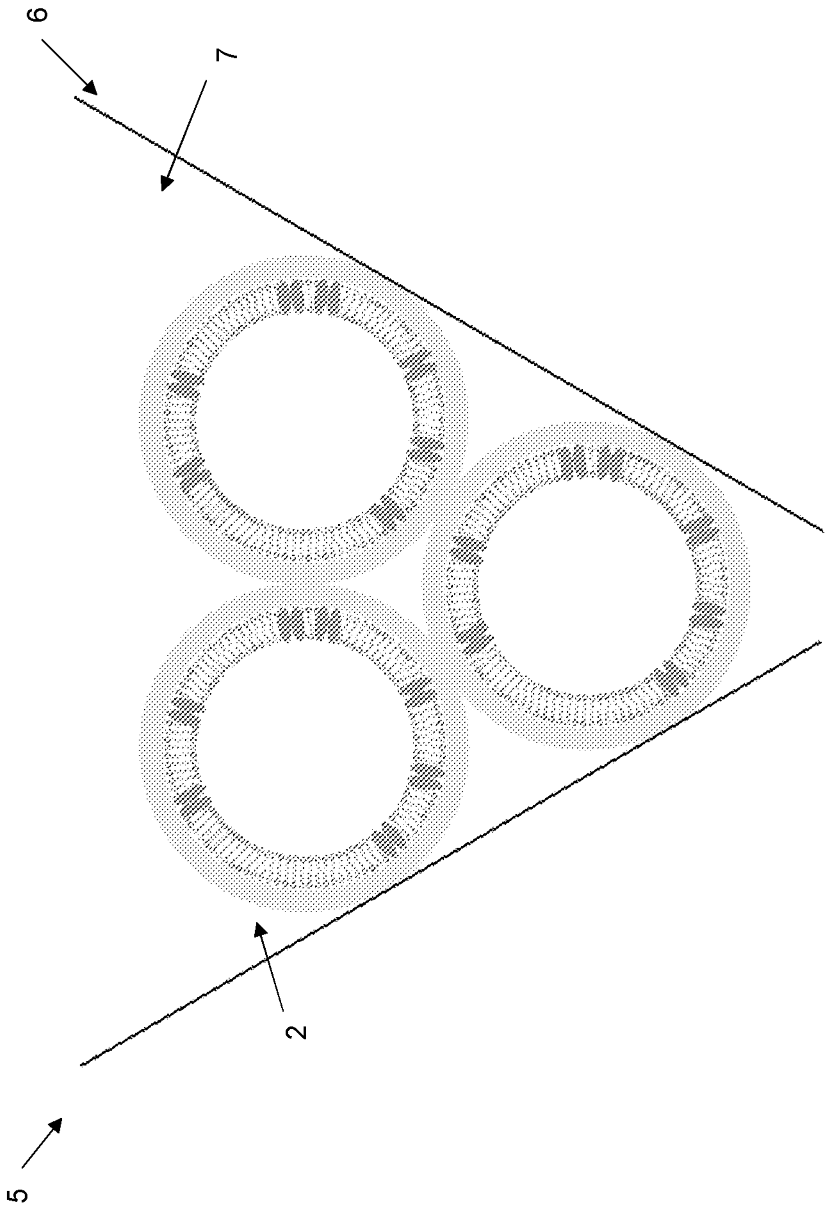
FIG. 9—Schematic illustration of a filtration device according to a further embodiment.

Another aspect of the invention relates to a filtration device 5, see FIGS. 7-9. The filtration device 5 comprises a porous support 6 comprising a plurality of pores 7 and macromolecule membrane structures 2 according to the embodiments.

In an embodiment, the macromolecule membrane structures 2 are provided on a surface of the porous support 6. In an exemplary embodiment, vesicles 2 containing water-channeling IMPs are introduced to a porous support 6 having surface-accessible pores 7 with pore widths in the range of, for instance, 0.5-50 nm. The vesicles 2 are adsorbed onto the porous support 6 and collapse into a single pore-spanning aquaporin-containing supported lipid bilayer or multiple aquaporin-containing supported lipid bilayers stacked on top of each other.

Alternatively, or in addition, the macromolecule membrane structures 2 are provided in the pores 7 of the porous support 6. Depending on the material of the porous support 6, the pores 7 may be ordered or disordered and either have well-defined pores 7 with a certain diameter, such as between 50 nm and 5000 nm, or be vaguely defined by a network structure. The pore width may be the same throughout the thickness of the porous support 6 or wider in one end of the porous support 6 compared to the other end. The pore width may also vary throughout the porous support 6 independent of position in the thickness. Vesicles 2 containing water-channeling IMPs 1 may be introduced to the pores 7 by placing a porous support 6 in a solution of the vesicles 2. External forces introduced by, for example, applying pressure or suction may or may not be used for successful introduction. In an example, the porous support 6 is placed in a filter holder that is connected to a syringe pump through tubing.

The porous support 6 together with the macromolecule membrane structures 2 form a filtration device 5 or filter that can be used to filter various liquids as is further disclosed herein. The coating of the membranes 3 with a silica layer 4 increases the stability of the macromolecule membrane structures 2 and the water-channeling IMPs 1 to enable them to be used for such filtering operations and still have sufficient operational or shelf life. This is otherwise a significant problem with the prior art biomimetic filtration devices.

The porous support 6 can be any support that is semipermeable, i.e., enables a filtrate to pass through the porous support 6 and the macromolecule membrane structures 2 present therein or thereon. The porous structure 6 should support the macromolecule membrane structures 2 but also be durable to the operation or process performed, such as be able to withstand certain pressures or chemical environments. The porous support may take any shape in order to comply with the operation or process performed, including a flat membrane, circular membrane, etc.

The porous support 6 may, in an embodiment, be manufactured from a polymer, a metal, an oxide of a metal, silicon dioxide, glass fiber, or a mixture thereof. Non-limiting, but illustrative, examples of polymer materials for the porous support 6 include polysulfone, polyethersulfone, polyphenylsulfone, polyetherethersulfone, polyetherketone, polyetheretherketone, polyphenylene ether, polydiphenylphenylene ether, cellulose, polyvinylene cellulose acetate, cellulose diacetate, cellulose triacetate, cellulose nitrate, polyphenylene sulfide, nitrocellulose, acetylated methylcellulose, polyacrylonitrile, polyvinylalcohol, polycarbonate, organic siloxane carbonate, polyestercarbonate, organic polysiloxane, polyethylene oxide, polyamide, polyimide, polyamidoimide, polybenzimidazole, polyolefin, polyacrylonitrile, nylon and a mixture thereof. Non-limiting, but illustrative, examples of metal (oxide) material for the porous support 6 include aluminum, aluminum oxide (alumina), titanium, titanium dioxide, zirconium, zirconium dioxide (zirconia), iron, iron oxide, and a mixture thereof.

The macromolecule membrane structures 2 may be provided onto the porous support 6 and/or in pores 7 of the porous support 6 in the form of a monolayer as shown in FIG. 8 or comprising a thicker layer of the macromolecule membrane structures 2 as shown in FIG. 7 typically containing multiple layers of macromolecule membrane structures 2.

Figure 10:
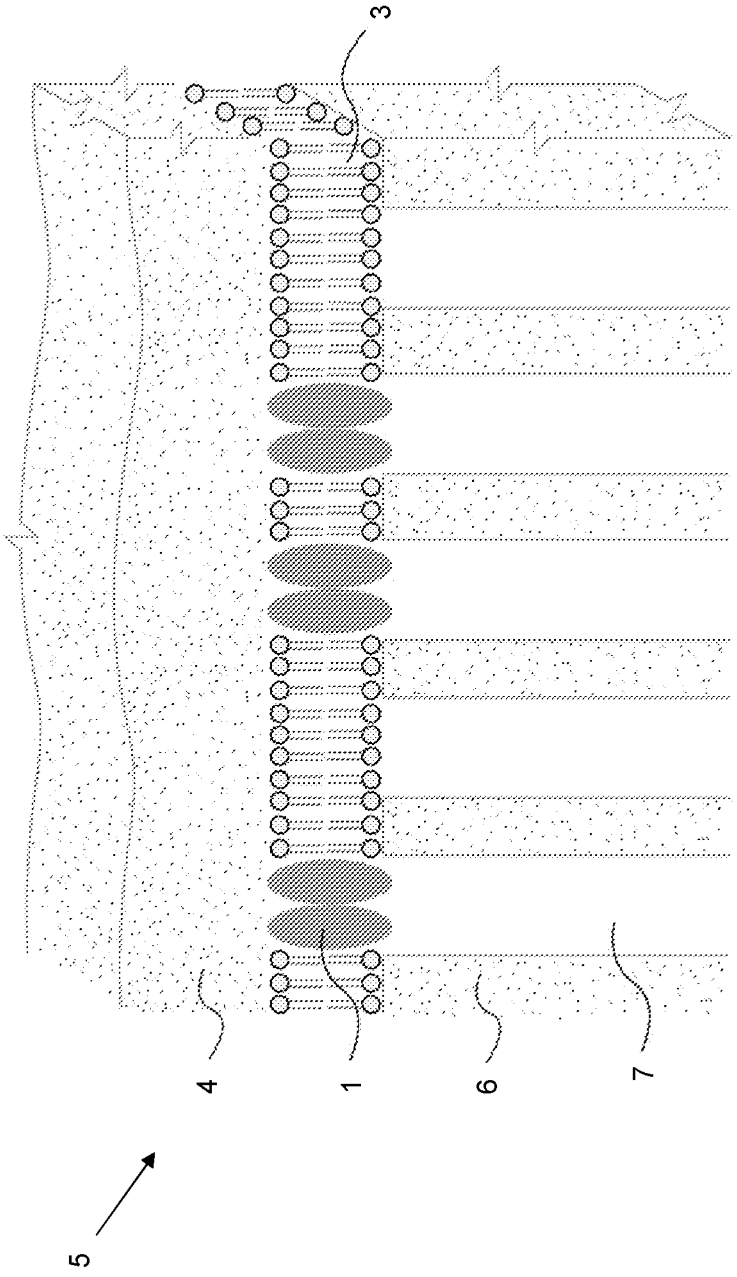
FIG. 10—Schematic illustration of a filtration device according to yet another embodiment.

FIG. 10 illustrates an embodiment of the filtration device 5, in which the 3 comprising water-channeling IMPs 1 is in the form of a planar structure deposited onto the porous support 6 comprises pores 7. A surface of the 3 opposite to the surface of the 3 facing the porous support 6 is coated with the silica layer 4.

If the silica layer 4 of the macromolecule membrane structures 2 is functionalized as previously described herein, the functionalized groups of the functionalized silica layer may link, such as covalently link, the macromolecule membrane structures 2 to the porous support 6. For instance, the functionalized groups can immobilize, attach and anchor the macromolecule membrane structures 2 to the wall of the pores 7 in the porous support 6 and/or onto an upper surface of the porous support 6.

In an embodiment, the macromolecule membrane structures 2 are coated with the silica layer 4 prior to depositing the macromolecule membrane structures 2 onto and/or into the porous support 6 of the filtration device 5. In another embodiment, the 3 comprising the water-channeling IMPs 2, such as in the form of proteoliposomes 2, are first deposited onto and/or into the porous support 6 and then the silicification process is performed to coat the proteoliposomes 2.

In this latter embodiment, the process for preparing the filtration device 5 comprises depositing a 3, such as a proteoliposome 2, comprising water-channeling IMPs 1 onto and/or into a porous support 6 and contacting the 3 comprising water-channeling IMPs 1 deposited onto and/or into the porous support 6 with a silica precursor to form a silica layer 4 coated on a first surface of the 3.

In an embodiment, the 3, such as in the form of a proteoliposome 2, could be immobilized or attached to the porous support 6 prior to the silicification process. In such an embodiment, the proteoliposome 2 could be connected and anchored to an upper surface of the porous support 6 and/or to walls in the pores 7 of the porous support 6. The attachment and immobilization can be achieved by linkers as disclosed in U.S. Pat. No. 9,943,812. Such linkers can be selected from the group consisting of a primary amine cross-linker, a sulfhydryl cross-linker, a carbohydrate cross-linker, a carboxyl cross-linker and a photoreactive cross-linker. The primary amine cross-linker could be imidoesters, N-hydroxysuccinimide ester, or glutaraldehyde, and the sulfhydryl cross-linker may be maleimide, haloacetyl, or pyridyldisulfide. The carbohydrate reactive cross-linker could be 1-(3-dimethylaminopropyl)-3-ethylcarbodiimide hydrochloride or 1,3-dicyclohexyl carbodiimide, and the photoreactive cross-linker may be aryl azide or diazirine.

The macromolecule membrane structure 2 and the filtration device 5 of the embodiments can be used in water purification to prepare a water filtrate. In such an application, an aqueous solution is filtered through the macromolecule membrane structure 2 or the filtration device 5 to obtain the water filtrate.

The aqueous solution could, for instance, be contaminated or polluted water, salt water or indeed any aqueous solution that should be filtrated or purified by removing the contamination or pollutions, such as salt ions, from the water to produce a pure water filtrate.

The macromolecule membrane structure 2 and the filtration device 5 of the embodiments can also be used in a method for concentrating a compound dissolved or dispersed in an aqueous solution. The method comprises filtering the aqueous solution through the macromolecule membrane structure 2 or the filtration device 5 to obtain a water filtrate lacking the compound and a retentate, also referred to as remaining feed in the art, comprising the compound at a higher concentration than the aqueous solution.

Hence, by filtering the aqueous solution through the macromolecule membrane structure 2 or the filtration device 5 a water filtrate is obtained and the retentate becomes concentrated with regard to the compound dissolved or dispersed therein.

Hence, once the macromolecule membrane structures 2 containing the water-channeling IMPs 1 are deposited, and optionally immobilized, onto and/or into the porous support 6, the resulting filtration device 5 may be useful in methods of water filtration to provide a pure water filtrate. This may be done using processes, such as forward osmosis, reverse osmosis or pressure retarded osmosis. The same setup may also be used for concentrating a solution of target molecules by removing excess water from the solution containing the target molecules.

Membranes 3 or vesicles 2 containing the water-channeling IMPs 1, including aquaporins 1, may be formed by incorporation of the water-channeling IMPs 1 into the membranes 3 or vesicles 2 through a process called reconstitution, which generally involves solubilizing the water-channeling IMPs 1 by using specific detergents, which assists in the removal of the water-channeling IMPs 1 from their source membranes while maintaining the integrity and biological function of the water-channeling IMPs 1. Once solubilized, the water-channeling IMPs 1 can be re-inserted into the target membranes 3 or vesicles 2 of interest.

Membranes 3 or vesicles 2 containing the water-channeling IMPs 1 may also be formed by transforming the source membranes into membranes 3 and vesicles 2, thus, retaining their natural environment as much as possible. Such transformation may be performed by extruding the source membranes through a porous filter with defined pore-size, thus downsizing the source membrane into small fragments and vesicles 2 of a certain size.

Examples

The present Example discloses a method to coat proteoliposomes in a thin layer of silica. More specifically, the passive water-transporter human aquaporin 4 (hAQP4) was reconstituted in phosphatidylcholine (POPC) liposomes, which were then coated with a thin layer of silica. The proteoliposome silicification process was monitored in detail to elucidate the mechanisms of silica shell growth. The secondary structure of hAQP4 was also monitored throughout the silicification process to provide an assessment of protein compatibility in this type of silicification.

hAQP4 Production in Pichia Pastoris and Protein Purification

Protein production in P. pastoris was performed following a protocol based on the production of geneoptimized hAQP4 [Nyblom et al., *Protein Expr. Purif.* 2007, 56(1): 110-120] resulting in a yield of more than 300 g of wet cells per liter culture. Cells were harvested by centrifugation (6000 g, 45 min, 4° C.) and stored at −20° C. For membrane preparation, 85 g of cells were thawed at 4° C. and resuspended in 200 mL breaking buffer (50 mM Tris-HCl pH 7.4 (Sigma-Aldrich) containing 150 mM NaCl (Sigma-Aldrich), 1 mM 2-mercaptoethanol (Fluka AG), and two EDTA-free cOmplete protease inhibitor cocktail tablets (Roche)). A Bead Beater (Bio Spec) was used to break the cells with 0.5 mm glass beads (Scientific industries), grinding for 12×30 s, with 60 s cool down between runs. Unbroken cells were collected by centrifugation (6000 g, 10 min, 4° C.) and crude membrane was harvested afterwards from the supernatant by ultracentrifugation (19000 g, 60 min, 4° C.). The resultant membrane was washed with urea buffer (4 M urea, 5 mM Tris-HCl pH 7.4, 2 mM EDTA, 2 mM EGTA) using a homogenizer and centrifuged again (19000 g, 60 min, 4° C.). The resulting pellet was homogenized and a sodium hydroxide wash was performed (20 mM NaOH) with a subsequent centrifugation step (19000 g, 60 min, 4° C.). A final wash was performed to remove traces of NaOH by homogenizing the membrane in membrane resuspension buffer (20 mM Tris-HCl pH 7.4, 250 mM NaCl, 1 mM 2-mercaptoethanol, 10% (w/v) glycerol). After a final centrifugation (19000 g, 60 min, 4° C.), the washed membrane pellet was resuspended in resuspension buffer at a concentration of about 400 mg membrane/ml.

Membrane solubilization of hAQP4 was carried out by mixing the membrane with solubilization buffer (25 mM Tris-HCl pH 7.4, 250 mM NaCl, 1 mM 2-mercaptoethanol, 10% (w/v) glycerol, 400 mM n-Octyl-β-Glucopyranoside (OG, analytical grade, Anatrace)) in a 1:1 volume ratio supplemented with EDTA-free protease inhibitor cocktail tablets. After gentle agitation for 90 min at 4° C., insolubilized material was removed by ultracentrifugation (19000 g, 60 min, 4° C.) and imidazole was given to the supernatant, so that the final concentration of imidazole corresponded to 50 mM.

For purification of hAQP4, the supernatant was loaded on a pre-equilibrated 5 ml Ni-NTA HisTrap HP column (GE Healthcare) and cycled for at least 2 hours. Equilibration of the column was done for three CV (20 mM Tris-HCl pH 7.4, 300 mM NaCl, 10% glycerol, 40 mM OG, 50 mM imidazole) before loading the supernatant. Non-specifically bound proteins were removed by washing the column matrix with 20 ml equilibration buffer. Protein was eluted with 20 ml elution buffer (20 mM Tris-HCl pH 7.4, 300 mM NaCl, 10% glycerol, 40 mM OG, 300 mM imidazole) and collected in fractions. Protein fractions were analyzed using SDS-PAGE and protein containing fractions were pooled together. A subsequent buffer exchange to storage buffer (25 mM citrate pH 6.0, 50 mM NaCl, 5% (w/v) glycerol, 40 mM OG, 2 mM DTT) was performed immediately thereafter. Finally, hAQP4 was concentrated to the final concentration of 9.7 mg/ml using a 50 kDa cut-off concentrator (Merck Millipore) and stored at −80° C.

Proteoliposome Preparation

Proteoliposomes were formed from POPC liposomes and purified hAQP4 in a reconstitution process. POPC (Avanti Polar Lipids Inc.) in chloroform (Sigma-Aldrich) was subjected to 3 h of rotary evaporation at 40° C. followed by the removal of residual chloroform under nitrogen. The lipid film was resuspended in reconstitution buffer (50 mM Tris-HCl, 50 mM NaCl, pH 8.0) at a concentration of 10 $mgml^{-1}$, prepared in $D_2O$ (99.8 atom % D, Sigma-Aldrich) for the SANS experiment (pH 8.4) and in Milli-Q water for the remaining experiments. For 1 ml of 4 $mgml^{-1}$ final lipid concentration in proteoliposomes, 400 µl of 10 $mgml^{-1}$ POPC in reconstitution buffer was mixed with 30 µl of 1 M NaCl (Sigma-Aldrich), 30 µl of 1 M Tris-HCl pH 8 (Sigma-Aldrich), and 430 µl of Milli-Q water. Then, 99 µl of 10% (w/v) n-octyl-p-D-glucoside was added by mixing followed by 5 min incubation. Then, 9.7 $mgml^{-1}$ purified hAQP4 was added in amounts resulting in final protein-to-lipid ratios (PLRs) of 1 hAQP4 to 6 POPC lipids (1:6) by mass for the CD measurements and 1:50 for the remaining experiments. The solution was gently mixed and incubated for 10 min at 20° C. Biobeads SM2 adsorbent (Bio-Rad laboratories) was equilibrated in reconstitution buffer and then added at a wet fraction of 30% (w/v) of the sample volume followed by 6-10 h of incubation at 20° C. on a rolling table in the dark. The biobeads were removed from the sample whereby the sample was centrifuged at 11000 rpm through a 0.2 µm spin column filter (WVR) prior to use.

Proteoliposome Characterization by DLS

DLS analyses were performed on 150 µl of 0.05 $mgml^{-1}$ lipid in liposome and proteoliposome samples using disposable UVette® cuvettes (Eppendorf) in a Malvern Zetasizer Nano ZS (Malvern) instrument at a fixed detection angle of 173°. The temperature was 20° C. and the presented data is the average from 3 repeats performed back-to-back.

Proteoliposome Silicification

Silicified liposomes and proteoliposomes were formed using 7.6 µl of tetraethylorthosilicate (TEOS, 98%, Sigma-Aldrich) added to 800 µl of 4 $mgml^{-1}$ liposomes and proteoliposomes in reconstitution buffer for all experiments except the time-resolved DLS and stopped-flow light scattering, where 3.8 µl of TEOS was added to 800 µl of 2 $mgml^{µ1}$ liposomes and proteoliposomes in reconstitution buffer. Silicification was conducted in glass vials without stirring for between 4 and 16 h in 25° C. in all cases except for the in situ SANS silicification kinetics experiment.

Characterization by TEM, STEM, SANS, DLS, Stopped-Flow Light Scattering and CD

For transmission electron microscopy (TEM) analysis, 2 μl droplets of 4 $mgml^{-1}$ silicified liposomes and proteoliposomes in reconstitution buffer were placed on Lacey carbon 300 Mesh Copper Grids (Ted Pella Inc.) and allowed to dry in ambient air. TEM analyses were performed using a FEI Titan 80-300 operating at 300 kV and a FEI Tecnai TF20 operating at 200 kV. Samples for scanning TEM (STEM) were prepared in the same way as for TEM and the STEM analysis was performed using a FEI Titan 80-300 operating at 300 kV.

Small-angle neutron scattering (SANS) experiments were performed at the D11 instrument in ILL (Institut Laue-Langevin, Grenoble, France) and at the KWS-1 instrument in FRM II (Research neutron source Heinz-Maier Leibnitz, Garching, Germany)

In FRM II, narrow quartz cells were used. No rotation was applied. 4 $mgml^{-1}$ of non-silicified and silicified sample were prepared in both Milli-Q water and $D_2O$. These samples were mixed to contrast match silica at an SLD of 3.47 and silicon at an SLD of 2.07. They were studied as is and there was also a "kinetics" study made where the proteoliposome sample was analyzed before, during and after silicification. λ=7 Å was used. The detector was positioned at 1.5 m, 8 m, and 20 m to span a wide q-range with good overlaps between the datasets. QtiKWS software was used to reduce and model the data.

In ILL, Hellma Analytics 120-QS quartz cells with 2 mm light path were used. They were mounted in a motorized holder that rotated the samples 5.5 revelations per minute in order to prevent sedimentation during the silicification process. 4 $mgml^{-1}$ proteoliposome sample in $D_2O$ was diluted to contrast match silica at an SLD of 3.47. Proteoliposomes that were silicified on beforehand as well as the process of silicifying proteoliposomes was studied. λ=5 Å was used to obtain as high intensity as possible. The detector was positioned at 1.4 m, 8 m, and 39 m to span a wide q-range with good overlaps between the datasets. Temperature was 25° C. for both SANS experiments. BerSANS software [Keiderling, *Appl. Phys. A-Mater. Sci. Process* 2002, 74: S1455-S1457] was used to reduce the data, whereas QtiKWS software was used to model the data.

Time-resolved DLS silicification analyses were performed on 150 μl of 2 $mgml^{-1}$ lipid in liposome and proteoliposome samples using disposable UVette® cuvettes (Eppendorf) in a Malvern Zetasizer Nano ZS (Malvern) instrument at a fixed detection angle of 173°. 3.8 μl of TEOS was added to 800 μl of 2 $mgml^{-1}$ liposomes and proteoliposomes in reconstitution buffer subsequent to the first DLS recording. Samples of 150 μl were analyzed by DLS every 30 minutes, upon which the sample was returned to the silicification vial. The temperature was 20° C. and the presented data is the average from 3 repeats performed back-to-back.

Time-resolved stopped-flow light scattering experiments were conducted through rapid mixing of 2 $mgml^{-1}$ liposome and proteoliposome silicification samples in reconstitution buffer (50 mM Tris-HCl, 50 mM NaCl, pH 8.0) with hyperosmolar solution (reconstitution buffer with 300 mM sucrose). 3.8 μl of TEOS was added to 800 μl of 2 $mgml^{-1}$ liposomes and proteoliposomes in reconstitution buffer subsequent to the first recording. The experiments were performed with 1 h intervals in an SFM 2000 (BioLogic Science Instruments) with each rapid mixing requiring 80 μL of sample and 80 μL of hyperosmolar buffer. The scattering was monitored at a fixed angle of 90°, and data was collected at a wavelength of 438 nm. The collected data was fitted to a two-exponential function in order to obtain rate constants of water transport, which are denoted as k-values.

Circular dichroism (CD) spectra were acquired on a Chirascan™ circular dichroism spectrometer with a Peltier temperature controller. The lamp, monochromator, and sample chamber were purged with $N_2$ (g) for 5 min before analysis at flow rates of 1 $lmin^{-1}$, 3 $lmin^{-1}$, and 1 $lmin^{-1}$, respectively. Spectra were recorded between 190 nm and 250 nm in a 1 mm pathlength quartz cuvette using a bandwidth of 1 nm and a time constant of 10 s. Data below 200 nm was omitted due to the buffer absorbance causing the high-tension voltage (HV) to exceed the threshold of 700 V below 198 nm. The presented data are averages from 3 scans recorded at 25° C. The data was subjected to background (pure buffer) subtractions prior to presentation. Measurements were conducted on 1 $mgml^{-1}$ lipid concentration, LPR 6 by mass in reconstitution buffer. CD data was normalized to the shift in applied HT voltage to account for the increase in absorption caused by the formation of silica shells.

Derivation of the SANS Model for Silicified Proteoliposomes

Figure 3:
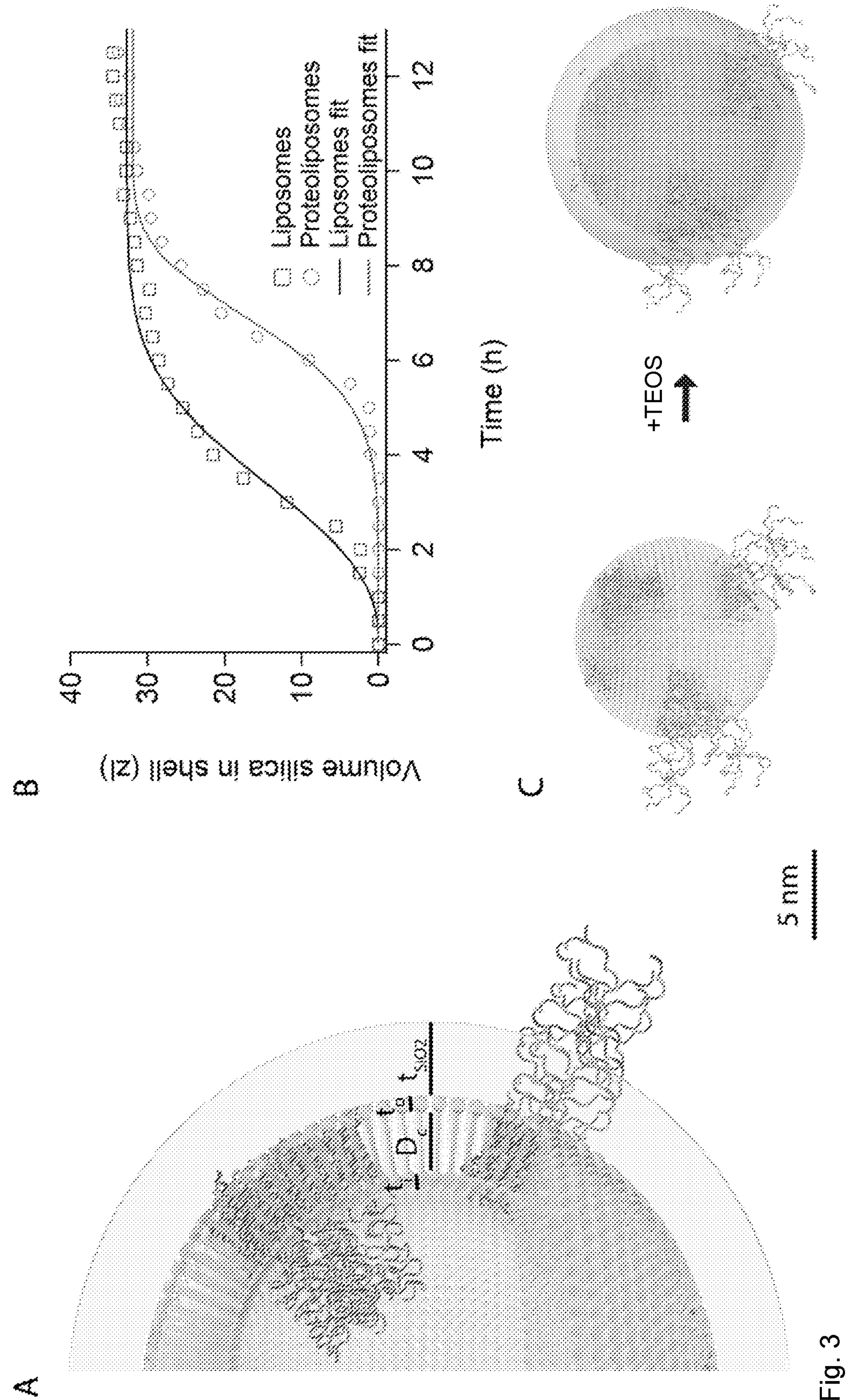
FIG. 3—(A) Illustration depicting a partly opened silicified hAQP4-containing proteoliposome with geometrical parameters assigned. $t_i$ represents the thickness of the inner leaflet lipid headgroups, $D_c$ represents the thickness of the hydrophobic lipid tails from both leaflets, $t_o$ represents the thickness of the outer leaflet lipid headgroups, and $t_{sio2}$ represents the thickness of the silica shell. (B) Comparison of deposited silica volumes as a function of time for liposome (squares) and proteoliposome (circles) silicification. The solid lines present fits to an Avrami-type equation. (C) Schematic illustration of the silicification process. hAQP4-containing proteoliposomes are mixed with the silica precursor TEOS, which results in the formation of a silica shell on the outside of the proteoliposome.

STEM analysis of silicified proteoliposomes indicate a core-shell structure where proteoliposomes are covered in a thin silica shell. The geometrical model parameters of the bilayer and the silica shell used for SANS data analysis are depicted in FIG. 3A. Each proteoliposome consists of an aquaporin-containing lipid bilayer of spherical geometry that envelops a liquid-filled core of radius $R_{core}$. The protein-containing lipid bilayer that makes up the shell of the proteoliposome is radially divided into 3 layers based on composition; an inner hydrophilic lipid head group region layer of thickness $t_i$, a hydrophobic lipid tail layer of thickness $D_c$, which includes the protein, and an outer hydrophilic head group layer of thickness $t_o$. The total radius of the proteoliposome is, thus, defined by the total radius at equator, $R_{tot}$, which is a sum of the core radius $R_{core}$ and the sum of thicknesses of the three layers in the lipid bilayer, $t_i$, $D_c$, and $t_o$. The model also includes a silica layer of thickness $t_{silica}$ that is situated on the outside of the lipid bilayer.

The total scattering intensity I(q) can thus be written as:

$$I(q) = \frac{\varphi}{V_{tot}} S(q) \cdot (A(q)_{core} \cdot \Delta\rho_{core} \cdot V_{core} + A(q)_i \cdot \Delta\rho_i \cdot V_i + A(q)_c \cdot \Delta\rho_c \cdot V_c + A(q)_o \cdot \Delta\rho_0 \cdot V_o + A(q)_{silica} \cdot \Delta\rho_{silica} \cdot V_{silica})^2$$

where φ is the volume fraction.

The scattering amplitude of the individual concentric spherical layers can be described by:

$$A(q)_i = \frac{(V_{core} + V_i) \cdot a(q, R_{core} + t_i) - V_{core} \cdot a(q, R_{core})}{V_i},$$

inner lipid head groups $$A(q)_c = \frac{(V_{core} + V_i + V_c) \cdot a(q, R_{core} + t_i + D_c) - (V_{core} + V_i) \cdot a(q, R_{core} + t_i)}{V_c},$$

lipid tails $$A(q)_o = \frac{V_{tot} \cdot a(q, R_{tot}) - (V_{core} + V_i + V_c) \cdot a(q, R_{core} + t_i + D_c)}{V_o},$$

-continued outer lipid head groups $$A(q)_{silica} = \frac{((V_{tot} + V_{silica}) \cdot a(q, R_{tot} + t_{silica}) - V_{tot} \cdot a(q, R_{tot}))}{V_{silica}},$$

silica layer where $a(q, x)=3\cdot(\sin(q\cdot x)-x\cdot q\cdot\cos(q\cdot x))/(q\cdot x)^3$ and the inner volume of the vesicle, $V_{core}$, is defined as $$V_{core}=4/3\pi\cdot R_{core}^3$$

the volume of the inner lipid head groups, $V_i$, is defined as $$V_i=4/3\cdot\pi\cdot((R_{core}+t_i)^3-R_{core}),$$

the volume of the lipid tails, $V_c$, is defined as $$V_c=4/3\cdot\pi\cdot((R_{core}+t_i+D_c)^3-(R_{core}+t_i+D_c)^3),$$

the volume of the outer lipid head groups, $V_o$, is defined as $$V_o=4/3\cdot\pi\cdot((R_{core}+t_i+D_c+t_o)^3-(R_{core}+t_i+D_c)^3),$$

the total volume of the proteoliposome, $V_{tot}$, defined as $$V_{tot}=4/3\cdot\pi\cdot((R_{core}+t_i+D_c+t_o)^3)$$

and the volume of the silica shell, $V_{silica}$, is defined as $$V_{silica}4/3\cdot\pi\cdot((R_{core}t_i+D_c+t_o+t_{silica})_3-(R_{core}+t_i+D_c+t_o)^3)$$

To account for the process of silica deposition on the proteoliposomes, $f_{silica}$ was introduced to denote the fraction of proteoliposomes covered in a silica shell. The parameter $f_{protein}$ was similarly used to denote the volume fraction of protein in the sample. Both silica and protein were allowed to exist in the inner lipid head groups layer ($f_{sil,i}$, $f_{prot,i}$), the lipid tail layer ($f_{sil,c}$, $f_{prot,c}$), and the outer lipid head groups layer ($f_{sil,o}$, $f_{prot,o}$) in proportions constrained to $$f_{x,i}+f_{x,c}+f_{x,0}=1$$

where the subscript x denotes sil or prot. The number of lipids in each proteoliposome, P, was calculated as $$P = \frac{V_c}{V_{tail}} \cdot (1 - f_{sil,c} \cdot f_{silica} - f_{prot,c} \cdot f_{protein})$$

where $V_{tail}$ is the volume of a lipid tail comprised of 2 hydrocarbon chains. Water was included as a component in the inner lipid head groups, the outer lipid head groups and the silica layer as $f_{w,i}$, $f_{w,o}$, and $f_{w,silica}$, respectively. The "dry volume" of the silicified proteoliposome was given by $$V_{tot}=V_i\cdot(1-f_{w,i})+V_c+V_o\cdot(1-f_{w,o})+V_{silica}\cdot(1-f_{w,silica})$$

The contrasts for the different layers are defined by $$\Delta\rho_i = \rho_{head} \cdot (1 - f_{prot,i} \cdot f_{protein} - f_{sil,i} \cdot f_{silica} - f_{w,i}) + \rho_{prot} \cdot f_{prot,i} \cdot f_{protein} + \rho_{silica} \cdot f_{sil,i} \cdot f_{silica} + \rho_{solvent} \cdot f_{w,i} - \rho_{solvent}$$

$$\Delta\rho_c = \rho_{tail} \cdot (1 - f_{prot,c} \cdot f_{protein} - f_{sil,c} \cdot f_{silica}) + \rho_{prot} \cdot f_{prot,c} \cdot f_{protein} + \rho_{silica} \cdot f_{sil,c} \cdot f_{silica} - \rho_{solvent}$$

$$\Delta\rho_o = \rho_{head} \cdot (1 - f_{prot,o} \cdot f_{protein} - f_{sil,o} \cdot f_{silica} - f_{w,o}) +$$

-continued $$\rho_{prot} \cdot f_{prot,o} \cdot f_{protein} + \rho_{silica} \cdot f_{sil,o} \cdot f_{silica} + \rho_{solvent} \cdot f_{w,o} - \rho_{solvent}$$

$$\Delta\rho_{silica} = \rho_{silica} \cdot (1 - f_{w,silica}) + \rho_{solvent} \cdot f_{w,silica} - \rho_{solvent}$$

where $\rho_{head}$, $\rho_{tail}$, $\rho_{silica}$ and $\rho_{solvent}$ are the scattering length densities (SLD) of the lipid head, lipid tail, silica, and bulk solvent, respectively.

Finally, the dry volume of silica deposited on each liposome/proteoliposome was calculated using $$V_{silica,dry}=4/3\cdot\pi\cdot((R_{core}+t_i+D_c+t_o+t_{silica})^3-(R_{core}+t_i+D_c+t_o)^3)\cdot(1-f_{w,silica})$$

Results

The structural characteristics of liposomes and proteoliposomes were assessed using DLS and SANS. Polydispersity indices (PDIs) were 0.15 for liposomes and 0.27 for proteoliposomes as determined by DLS. The broadness of the SANS peak corresponding to vesicle size (located around $2\cdot10^{-3}$ Å$^{-1}$) also suggested sample size polydispersity. Liposomes and proteoliposomes had Z-avg diameters of 124.8 nm±2.9 nm and 132.9±7.0 nm, respectively. The data was also weighted according to number to compensate for non-proportional light scattering contributions from large vesicles, which were clearly present due to the polydispersity of both samples. The weighted average diameters then became 78.0 nm±5.1 nm for liposomes and 66.0 nm±3.2 nm for proteoliposomes.

SANS characterization of samples prior to silica precursor addition was performed in two contrasts, which were contrast-matched to the scattering length densities (SLD) of $D_2O$ and silica ($CMSiO_2$). Simultaneous fitting of these contrasts to a custom-designed core-multi-shell model resulted in diameters of 45 nm, inner lipid head group thicknesses of 9 Å, and lipid tail layer thicknesses of 34 Å for both liposomes and proteoliposomes. The thickness of the outer lipid head groups was 10 Å for liposomes and 12 Å for proteoliposomes.

SANS was used to study the silicification process and the evolution of the silica shell to elucidate how liposomes and proteoliposomes were affected in the process. Sizes and compositions of the bilayer compartments and the silica shell were obtained. SANS profiles acquired during the course of proteoliposome silicification is presented in FIG. 2A. Plausible fits to the silicification process were obtained by varying five fit parameters; concentration of species in the neutron beam (conc.), fraction of silica coated liposomes/proteoliposomes ($f_{silica}$), outer lipid head group thickness ($t_o$), silica shell thickness ($t_{silica}$), and the water content in the silica shell ($t_{silica}$). Initial and final fit values on selected parameters along with the dry volume of the silica shell ($V_{silica,\ dry}$, derived using Equation 1) are presented in Table 2.

$$V_{silica,dry}=4/3\cdot\pi\cdot((R_{core}+t_i+D_c+t_o+t_{silica})^3-(R_{core}+t_i+D_c+t_o)^3)\cdot(1-f_{w,silica}) \quad \text{(Equation 1)}$$

$V_{silica}$, dry is also presented as a function of time in FIG. 3B. The data presented in FIG. 3B was fitted to the Avrami-type growth function [Avrami, *J. Chem. Phys.* 1940, 8: 212-224 and Avram, *J. Chem. Phys.* 1941, 9(2): 177-184]:

$$V(t)=V_{initial}+(V_{final}-V_{initial})\cdot(1-e^{-k\cdot t^{\beta}}) \quad \text{(Equation 2)}$$

where $V_{intital}$ is the initial volume, $V_{final}$ is the final volume, k is the rate constant of silica formation, and β is the Avrami exponent. Fitting the silicification processes of liposomes and proteoliposomes using MATLAB® software returned the values presented in Table 3, whereas a formation mechanism based on these data is illustrated in FIGS. 3A and 3C. A silica formation half-time parameter ($t_{1/2}$) was introduced as a means to compare the liposome and proteoliposome fits despite their different Avrami exponents. The analysis was performed using the equation $$k_n(T) = \frac{\ln 2}{t_{1/2}^{\beta}} \quad \text{(Equation 3)}$$

where values on $k_n(T)$ and β were obtained from the fits.

Figure 11:
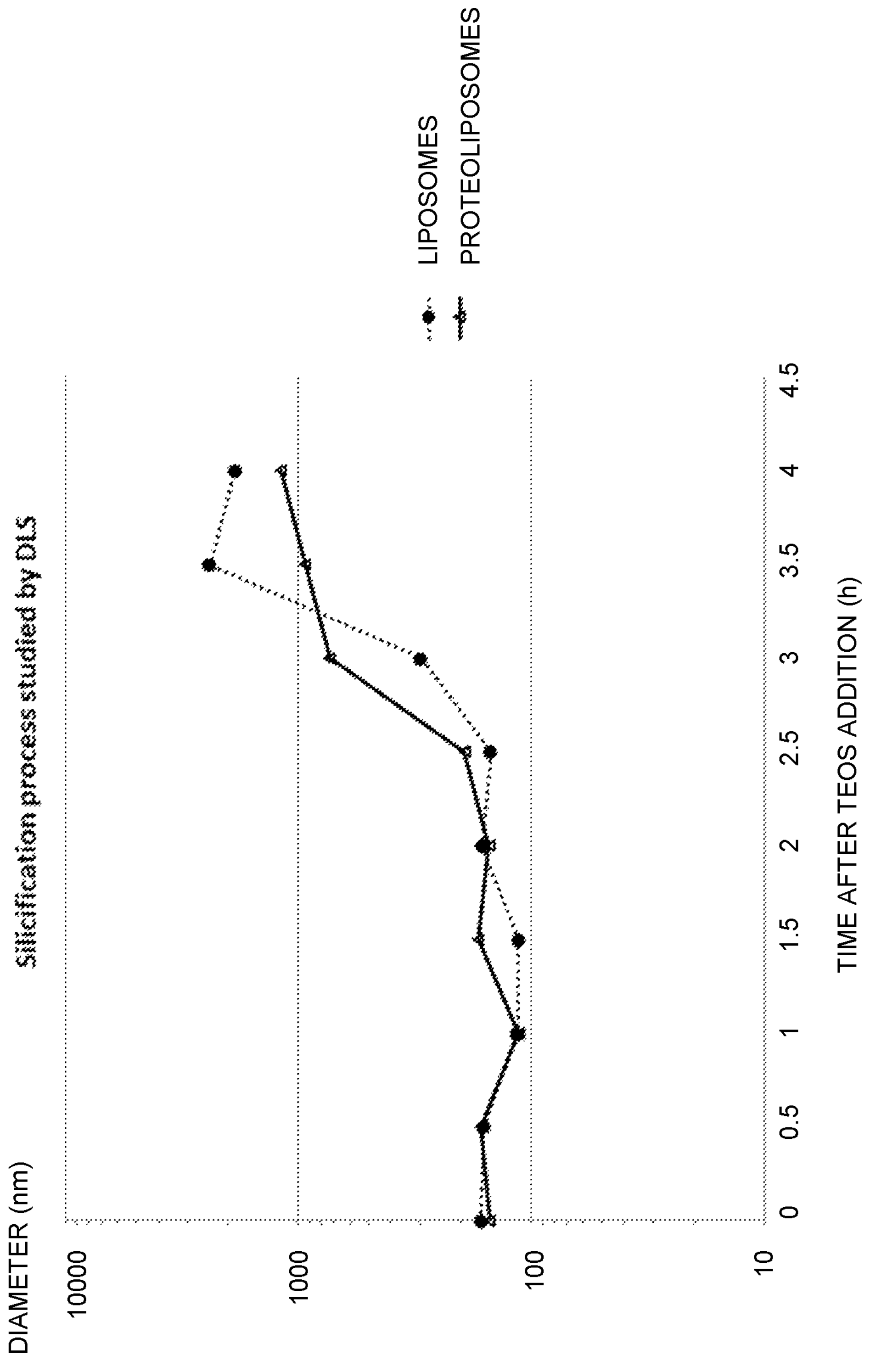
FIG. 11—Time-resolved dynamic light scattering (DLS) was used to study the aggregation behavior of liposomes and proteoliposomes during the silification process.

Time-resolved DLS was utilized to study the aggregation behavior of liposomes and proteoliposomes during the silicification process. The scattered light intensity started to increase after about 3 h of silicification in both the liposome and the proteoliposome samples (FIG. 11). This increase in scattering is attributed to aggregation of silicified liposomes and proteoliposomes.

Aquaporin functionality during the silicification process and upon silicification was assessed using time-resolved stopped-flow light scattering. As can be seen in Table 1, the proteoliposomes to a high degree retain their water transport capacity upon silicification as verified by the small change in k-value. The lipid membrane itself seems to become slightly more water permeable. The relatively low $R^2$ values obtained from the 10 h fits are attributed to a lower signal-to-noise ratio of vesicle shrinkage due to the presence of large aggregates.

TABLE 1 k-values obtained using time-resolved stopped-flow light scattering

| k-values ($s^{-1}$) | Liposomes | Proteoliposomes |
|---|---|---|
| 0 h | 11 (adj. $R^2$ = 1.00) | 36 (adj. $R^2$ = 1.00) |
| 1 h | 16 (adj. $R^2$ = 0.99) | 35 (adj. $R^2$ = 1.00) |
| 10 h | 18 (adj. $R^2$ = 0.73) | 31 (adj. $R^2$ = 0.84) |

Figure 2:
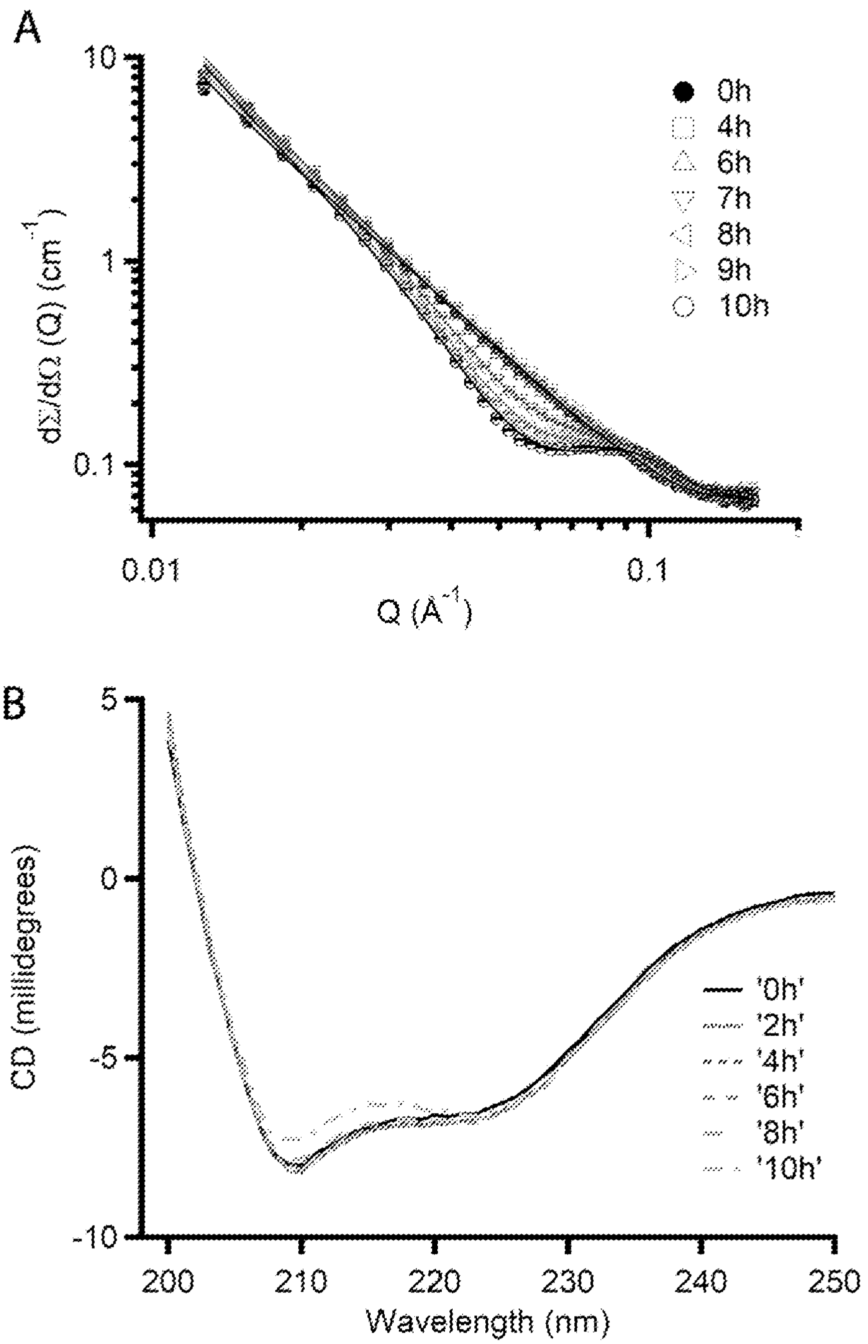
FIG. 2—(A) SANS profiles showing the hAQP4-containing proteoliposome silicification process. (B) CD spectra of hAQP4 during proteoliposome silicification.

The effect of silicification on hAQP4 secondary structure was assessed using CD (FIG. 2B). The results show that the predominantly α-helical native secondary structure of the protein was largely conserved upon silicification.

TABLE 2

Selected SANS fit parameter values obtained before and after silicification

| | Liposome silicification start | Liposome silicification end | Proteoliposome silicification start | Proteoliposome silicification end |
|---|---|---|---|---|
| Time (h) | 0 | 12 | 0 | 12 |
| $R_i$ (Å) | 225.3 | 225.3 | 225.3 | 225.3 |
| $t_i$ (Å) | 9.0 | 9.0 | 9.0 | 9.0 |
| $t_o$ (Å) | 10.0 | 13.8 | 12.0 | 17.6 |
| $D_c$ (Å) | 34.0 | 34.0 | 34.0 | 34.0 |
| $f_{SiO2}$ | 0.0 | 1.0 | 0.0 | 1.0 |
| c (mg/ml) | 1.29 | 1.47 | 1.16 | 1.84 |
| $f_{unilamellar}$ | 0.93 | 0.93 | 0.93 | 0.93 |
| $N_u$ | 1.4 | 1.4 | 1.4 | 1.4 |
| N | 3.8 | 3.8 | 3.8 | 3.8 |
| d (Å) | 67.0 | 67.0 | 65.4 | 65.4 |
| $fw_{SiO2}$ | 0.00 | 0.31 | 0.00 | 0.22 |
| $t_{SiO2}$ (Å) | 0.0 | 42.8 | 0.0 | 35.2 |
| $V_{silica,dry}$ (zl) | 0.0 | 34.5 | 0.0 | 32.4 |

TABLE 3

Exponential fit values for the volumetric silica shell growth on liposomes and proteoliposomes, including half-time of silica shell growth derived from fit values.

| | $V_{silica,dry,i}$(zl) | $V_{silica,dry,f}$(zl) | k | β | $t_{1/2}$(h) | $R^2$adj |
|---|---|---|---|---|---|---|
| Lipsome silicification | 0 | 32.7 | 0.24 | 2.4 | 3.62 | 0.987 |
| Proteolipsome silicification | 0 | 31.9 | 0.14 | 5.8 | 6.76 | 0.992 |

Silica-coated liposomes and proteoliposomes were studied using TEM upon complete silicification and drying. Results collected using TEM (FIGS. 4A, 4B) and STEM (FIGS. 4C, 4D) further described the geometrical and compositional characteristics of the silicified samples. STEM characterization shows that the silicified liposomes and proteoliposomes predominantly adapt a core-shell architecture.

Figure 5:
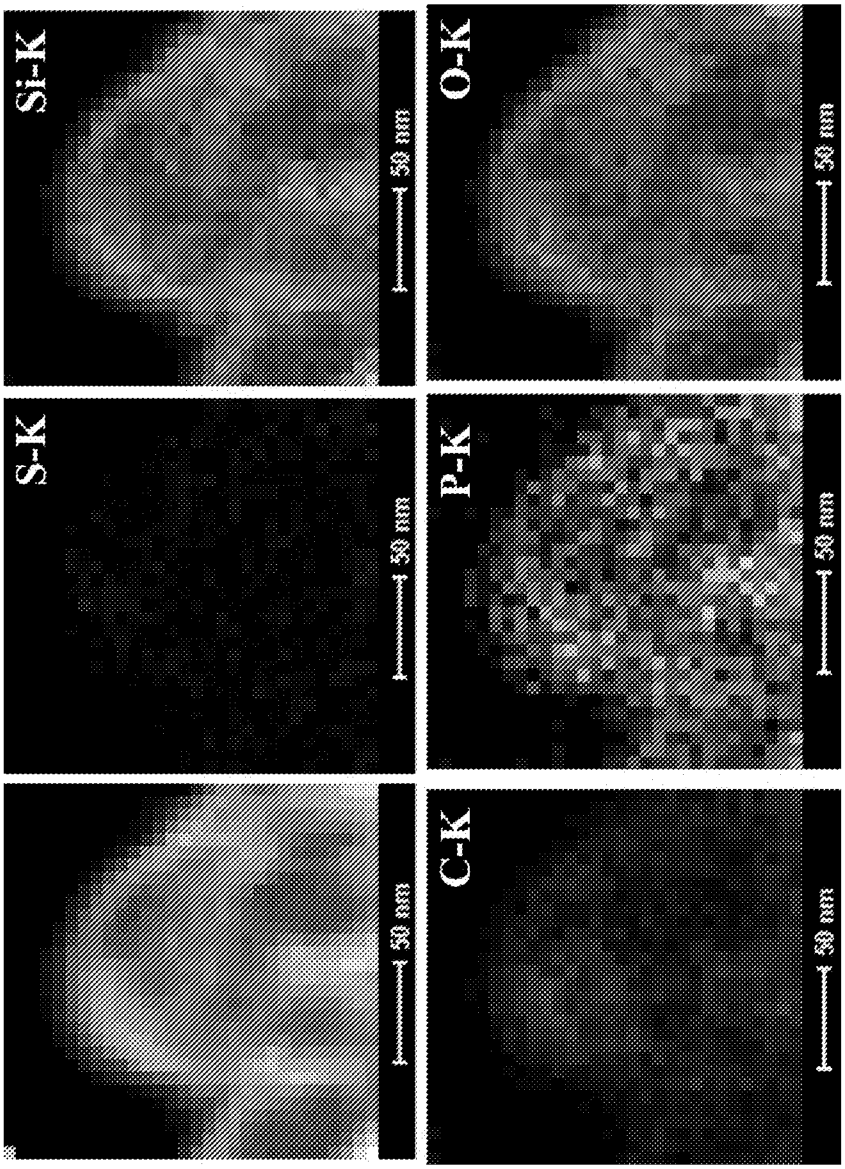
FIG. 5—Scanning transmission electron microscopy energy-dispersive X-ray spectroscopy (STEM-EDX) imaging was performed on dried silicified vesicles containing aquaporin. Elemental maps of sulfur (only present in aquaporin), silicon, carbon, phosphorous (only present in POPC lipid), and oxygen were obtained. Elemental maps of individual elements pinpointed the location of these elements in silicified vesicles containing aquaporin. It was shown that all of these elements were preferentially located in the bilayer and its associated silica coating. STEM high-angle annular dark-field (HAADF) micrograph of the same sample area is inserted in the top left position.

Silicified proteoliposomes were also subjected to elemental mapping. STEM energy-dispersive X-ray spectroscopy (EDX) was used to localize different elements as can be seen in FIG. 5, with a STEM high-angle annular dark-field (HAADF) micrograph of the same sample area also inserted. The results suggested that the visualized elements were more abundant along the silicified aquaporin-containing lipid bilayers lining the proteoliposomes.

Figure 6:
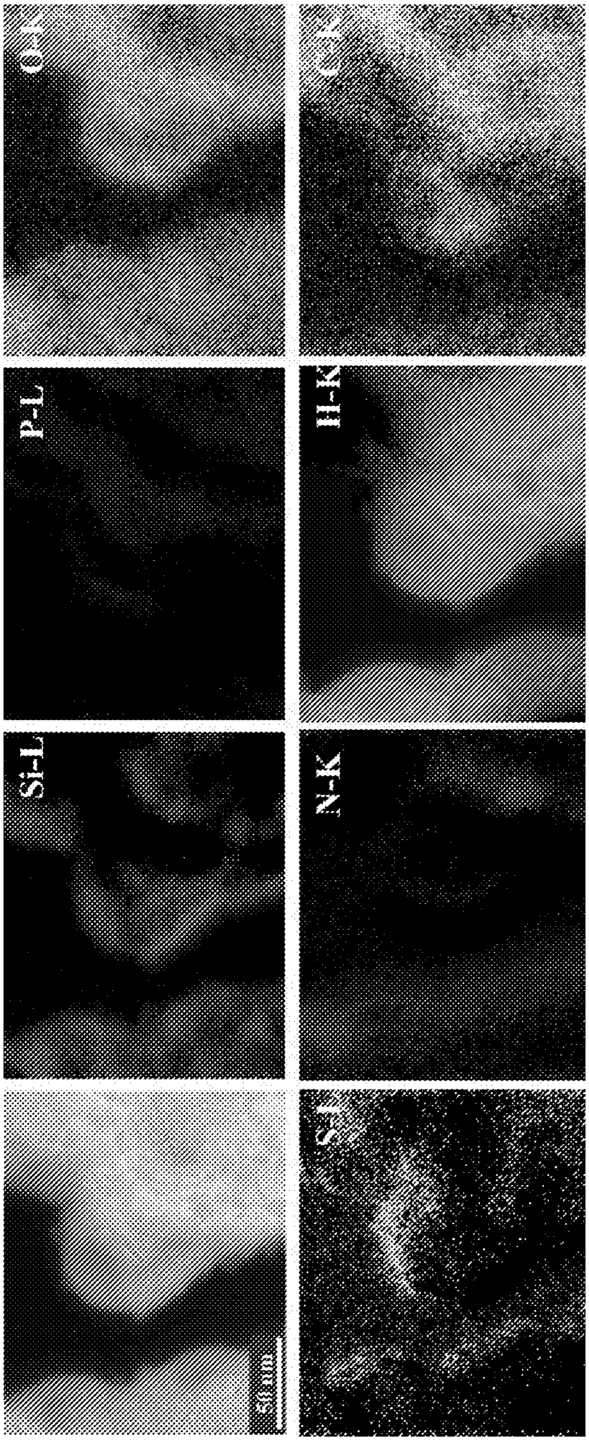
FIG. 6—Energy-filtered transmission electron microscopy (EFTEM) was used as a complementary method to STEM-EDX for localization of specific elements in dried silicified vesicles containing aquaporin. EFTEM was able to map both nitrogen and hydrogen in addition to the elements mapped by STEM-EDX due to an increased sensitivity for lighter elements. EFTEM confirmed the STEM-EDX results in that all of the relevant elements were preferentially located in the bilayer and its associated silica coating. The plasmon filtered EFTEM image of the same sample area is inserted in the top left position.

Additional elemental mapping was performed using energy filtered (EF) TEM. It is more sensitive to lighter elements as compared to EDX and it was therefore able to detect both nitrogen and hydrogen in addition to sulfur, silicon, carbon, phosphorous, and oxygen (FIG. 6).

SANS data modelling revealed that most of the parameters used to describe the systems remained constant during both liposome and proteoliposome silicification. In fact, changes in the same 5 parameters ($t_o$, $f_{silica}$, conc., $t_{silica}$, and $f_{w,\ silica}$) were sufficient to describe the changes in both samples accurately. In the model, concentration (conc.) was used as a floating parameter, directly interconnected with other parameters. The fraction of silica-coated liposomes/proteoliposomes ($f_{silica}$) remained constant at 0 for the initial 1 h and 3.5 h of liposome and proteoliposome silicification, respectively. This "lag phase" related to alkoxide precursor hydrolysis, during which TEOS ester bonds were cleaved to eventually form silicic acid and ethanol. At pH 8, this process is expected to progress slowly since the hydrolysis reaction is acid and base catalyzed.

Following precursor hydrolysis, $f_{silica}$ increased to 1 during periods of 1.5 h and 3 h for liposomes and proteoliposomes, respectively. This indicated that silica deposition took place within a confined time frame, rather than continuously throughout the duration of silicification. An interesting observation was that the thickness of the silica shell did not increase linearly with time. Instead, a layer on the order of the lipid bilayer thickness (~4 nm), composed of silicic acid and buffer, was arranged on liposomes and proteoliposomes as soon as deposition started. The liposomes and proteoliposomes (not including the silica shell) remained unaltered apart from the outer lipid head group layer that experienced swelling. The outer leaflet of the lipid bilayer is in direct contact with the deposited silicic acid and, hence, susceptible to alterations in the surrounding environment. According to the model, the outer lipid headgroup layer in the template samples consisted of 82% and 86% buffer for liposomes and proteoliposomes, respectively. Silicic acid interacted closely with the outer lipid head group layer, especially considering the high fraction of buffer in the initially deposited silicic acid layer (96% buffer in liposomes and 98% in proteoliposomes by the onset of deposition). The overall thickening of $t_o$ could be attributed to the existence of an interfacial water layer between the lipid bilayer and the silica shell.

Neither $t_o$ nor $t_{silica}$ exhibited a steady increase or decrease throughout the entire process in either sample, with minor deflections interrupting the overall patterns. Equation 1 was therefore adopted to study silica shell growth kinetics by connecting $t_o$ and $t_{silica}$ to the remaining geometric parameters and $f_{w,\ silica}$. The volume of the silica shell without buffer, $V_{silica,\ dry}$, as a function of time is presented in FIG. 3B. Changes in silica shell volume with time follows a sigmoidal pattern that was fitted to an Avrami-type growth function (Equation 2), originally derived for phase transformation processes, in particular crystallization. Different lengths of the lag phases resulted in different Avrami parameters, β, for silicification of liposomes and proteoliposomes. Therefore, comparison of the reaction rates, k, was not straightforward. Hence, the half-time of silicification ($t_{1/2}$) was calculated to accommodate for differences in β (Equation 3). As shown in Table 3, proteoliposome silicification had almost twice the $t_{1/2}$ of liposome silicification, which means that liposome silicification reached half the plateau volume in slightly less than half the time of proteoliposome silicification. Since $t_{1/2}$ is a compound measure of the lag phase and the start of the exponential phase, another approach was also utilized for the sake of comparison. Both shell growth processes were plotted from the onset of exponential growth, excluding the initial precursor hydrolysis phase. The growth phases were strikingly similar. It was therefore concluded that the difference in silicification of liposomes and proteoliposomes occured within the first, i.e., precursor hydrolysis, part of the process. Since the only difference between the samples was the protein, the presence of protein altered the formation mechanism of the silica shell. There are two main protein characteristics that may affect silica shell formation; electrostatic repulsion and steric hindrance. Since POPC lipids are zwitterionic, they are neutral at pH 8. hAQP4 on the other hand carries a slightly negative net charge owing to the isoelectric point of 7.6. As TEOS is hydrolysed into silicic acid, a small fraction of the silicic acid is ionized and therefore negatively charged. Hence, the slightly negative net charge of the protein will introduce electrostatic repulsion that may hinder some of the silicic acid to access the lipid bilayer head groups. This is, however, not very likely to be the only explanation, especially since the silica shell interacts with the lipid head groups through hydrogen bonding to the negatively charged phosphatidyl moiety rather than to the positively charged choline moiety. Steric hindrance is, hence, presented as the more likely option, perhaps in combination with electrostatic repulsion. The C-terminal domain of hAQP4 reaches out into the bulk, likely causing proteoliposomes to not come into direct contact. This also seemed to be the case for silicified proteoliposomes, that did not aggregate to the same extent as silicified liposomes. Steric hindrance could explain the extended lag phase of proteoliposome silicification in terms of poorer accessibility for the silicic acid to the lipids.

Figure 4:
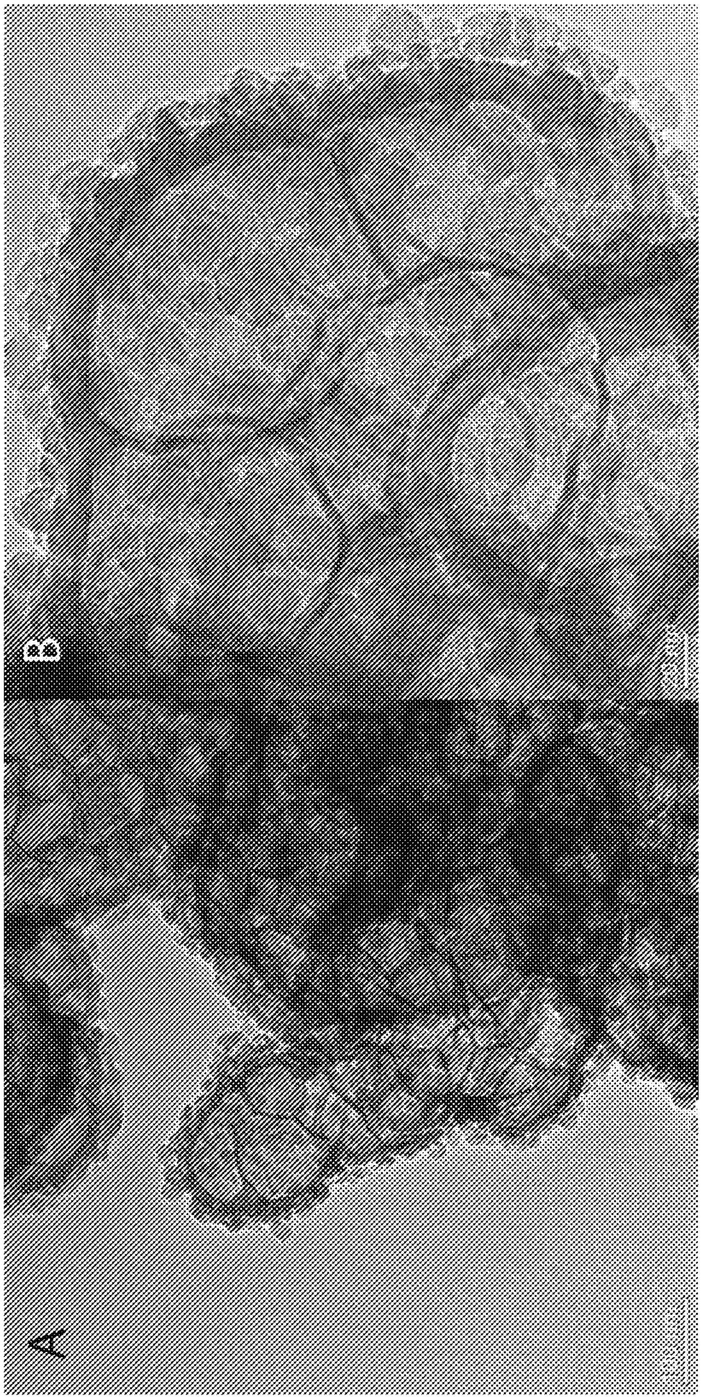
FIG. 4—TEM micrographs of silicified hAQP4-containing POPC proteoliposomes in (A) lower and (B) higher magnification. Dark lines depict silicified aquaporin-containing lipid bilayers and brighter areas enclosed by or associated with the aquaporin-containing lipid bilayers depict silica. (C) and (D) show STEM micrographs of silicified proteoliposomes where silica depositions are depicted as bright features.
Figure 4:
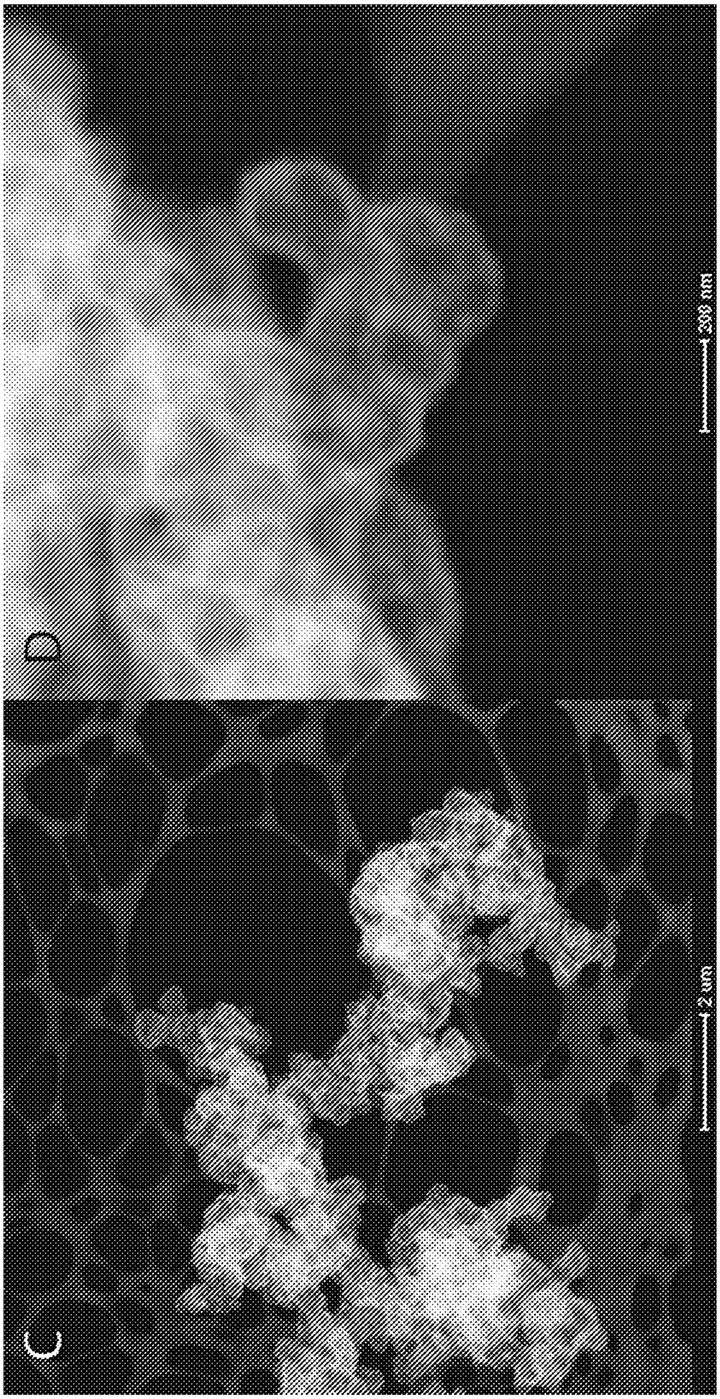

A similarity between liposome and proteoliposome silicification was the thickness of the silica shell, which became around 4 nm using these formation conditions. Interestingly, there were smaller silica particles present in the silicified and dried samples, which were clearly seen in TEM (FIG. 4B). This indicated that there was more material available than what was consumed in forming the silica shell. For both samples, the majority of the silica formation seemed to have occurred at the bilayer (FIG. 4). It was also of interest to study the arrangement of other elements upon silicification to get an indication on how the original proteoliposome composition was altered. STEM-EDX indicated that the detected elements were most abundant along the silica lining of the proteoliposomes, which indicated that the aquaporin-containing lipid bilayer was intact. Since the mapping was done in transmission mode, the maps showed the 2D-projection of the 3D sample and elements were therefore detected in other parts of the silicified proteoliposomes as well, albeit in lower concentrations. Complementary element mapping was conducted using EFTEM, which is more sensitive to lighter elements. It was, in addition to the elements detected by EDX, therefore also able to detect nitrogen and hydrogen, which are common components in biological materials. EFTEM elemental mapping confirmed the indications provided in using EDX; elements related to the aquaporin-containing lipid bilayer were enriched in the silicified regions lining the proteoliposomes.

CD studies revealed that the protein remained intact throughout the silicification process (FIG. 2B). Changes in protein structure helicity is typically assessed by changes to the absorption 222 nm absorption band, which corresponds to the n→π* transition in peptide bonds. As judged from the CD data, the absorption at 222 nm was almost identical, meaning that the transmembrane part of hAPQ4 was intact. The hydrophobic tail region of the lipid bilayer, hence, remained the same, resulting in a retained protein secondary structure. The reason for the small change in amplitude at 209 nm could be small modifications to the disordered parts of the protein, which would be reasonable since some of those parts are exposed to the silica.

This example disclosed a method to stabilize hAQP4-containing proteoliposomes by coating in a thin silica shell. Importantly, the native conformation of the proteins was maintained upon silicification.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

The invention claimed is:

1. A macromolecule membrane structure comprising:
a membrane that includes water-channeling integral membrane proteins; and
a silica layer that is on a first surface of the membrane, wherein the membrane is a proteoliposome or a proteopolymersome, and
wherein the first surface of the membrane is the outer surface of the proteoliposome or proteopolymersome.

2. The macromolecule membrane structure according to claim 1, wherein the membrane is a bilayer membrane comprising amphiphilic molecules.

3. The macromolecule membrane structure according to claim 2, wherein the membrane is a lipid bilayer membrane that comprises amphiphilic lipids selected from the group consisting of phosphatidylcholine, phosphatidylserine, phosphatidylethanolamine, phosphatidylglycerol, phosphatidylinositol, cardiolipin, cholesterol, sphingomyelin, asolectin, diphytanoylphosphatidylcholine (DPhPC), 1,2-dipalmitoyl-sn-glycero-3-phosphocholine (DPPC), 1,2-diheptanoyl-sn-glycero-3-phosphocholine (DHPC), 1,2-dihexanoyl-sn-glycero-3-phosphoethanolamine (DHPE), 1,2-dimyristoyl-sn-glycero-3-phosphocholine (DMPC), dimyristoyl phosphatidylserine (DMPS), dimyristoyl phosphatidylglycerol, dilauroyl phosphatidycholine (DLPC), 1,2-dimyristoyl-sn-glycero-3-phosphoethanolamine (DMPE), 1,2-dimyristoyl-sn-glycero-3-[phospho-rac-(1-glycerol)] (DMPG), lyso phosphocholine (PC), lyso PE, 1,2-didecanoyl-sn-glycero-3-phosphocholine (DDPC), 1,2-dierucoyl-sn-glycero-3-phosphate (DEPA), 1,2-erucoyl-sn-glycero-3-phosphocholine (DEPC), 1,2-dierucoyi-sn-alycero-3-phosphoethanolamine (DEPE), 1,2-linoleoyl-sn-glycero-3-phosphocholine (DLOPC), 1,2-dilauroyl-sn-glycero-3-phosphate (DLPA), 1,2-dilauroyl-sn-glycerco-3-phosphoethanolamine (DLPE), 1,2-dilauroyl-sn-glycero-3-phosphoserine (DLPS), 1,2-dimyristoyl-sn-glycero-3-phosphate (DMPA), 1,2-dimyristoyl-sn-glycero-3-phosphoserine (DMPS), 1,2-dioleoyl-sn-glycero-3-phosphate (DOPA), 1,2-oleoyl-sn-glycero-3-phosphocholine (DOPC), 1,2-dioleoyl-sn-glycero-3-phosphoethanolamine (DOPE), 1,2-dioleoyl-sn-glycero-3-phosphoserine (DOPS), 1,2-dipalmitoyl-sn-glycero-3-phosphate (DPPA), 1,2-dipalmitoyl-sn-glycero-3-phosphoethanolamine (DPPE), 1,2-dipalmitoyl-sn-glycerco-3-phosphoserine (DPPS), 1,2-distearoyl-sn-glycero-3-phosphate (DSPA), 1,2-distearoyl-sn-glycero-3-phosphocholine (DSPC), 1,2-diostearpyl-sn-glycero-3-phosphoethanolamine (DSPE), 1-myristoyl-2-stearoyl-sn-glycero-3-phosphocholine (MSPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-oleoyl-sn-glycero-3-phosphoethanolamine (POPE), 1-palmitoyl-2-stearoyl-sn-glycero-3-phosphocholine (PSPC), 1-stearoyl-2-myristoyl-sn-glycero-3-phosphocholine (SMPC), 1-stearoyl-2-oleoyl-sn-glycero-3-phosphocholine (SOPC), 1-stearoyl-2-palmitoyl-sn-glycero-3-phosphocholine (SPPC), a lipid from a cell membrane, a lipid from an organelle, a cross-linkable lipid, and a mixture thereof.

4. The macromolecule membrane structure according to claim 2, wherein the amphiphilic molecules are selected from amphiphilic AB, ABA and ABC copolymers, and mixtures thereof.

5. The macromolecule membrane structure according to claim 1, wherein the water-channeling integral membrane proteins are aquaporins.

6. The macromolecule membrane structure according to claim 1, wherein the silica layer has an average thickness in a range of from 0.1 nm to 1000 nm.

7. The macromolecule membrane structure according to claim 1, wherein the water-channeling integral membrane proteins are capable of channeling water through the membrane in the presence of the silica layer.

8. The macromolecule membrane structure according to claim 1, wherein the silica layer is a functionalized silica layer.

9. A filtration device comprising:
a porous support comprising a plurality of pores; and
the macromolecule membrane structure according to claim 1.

10. The filtration device according to claim 9, wherein the macromolecule membrane structure is provided on a surface of the porous support and/or in a pore of the porous support.

11. The filtration device according to claim 9, wherein the porous support comprises a material selected from the group consisting of a polymer, a metal, an oxide of the metal, a silicon dioxide, a glass fiber, and a mixture thereof.

12. The filtration device according to claim 9, wherein functional groups of the silica layer link the macromolecule membrane structure to the porous support.

13. A method of preparing a water filtrate, the method comprising filtering an aqueous solution through the macromolecule membrane structure according to claim 1 to obtain the water filtrate.

14. A method for concentrating a compound dissolved or dispersed in an aqueous solution, the method comprising filtering the aqueous solution through the macromolecule membrane structure according to claim 1 to obtain a water filtrate lacking the compound and a retentate comprising the compound at a higher concentration than the aqueous solution.

15. The macromolecule membrane structure according to claim 5, wherein the aquaporins are selected from the group consisting of a human aquaporin (hAQP), a bovine aquaporin, a fish aquaporin, a yeast aquaporin, a plant aquaporin, a bacterial aquaporin, and a mixture thereof.

16. The macromolecule membrane structure according to claim 1, wherein the silica layer has an average thickness in a range of from 1 nm to 100 nm.

17. The macromolecule membrane structure according to claim 8, wherein the functionalized silica layer comprises a silane, an alkoxysilane, hexamethyldisilazane (HMDZ), or a combination thereof.

18. A process for preparation of the macromolecule membrane structure of claim 1, the process comprising contacting the membrane comprising the water-channeling integral membrane proteins with a silica precursor to form the silica layer on the first surface of the membrane.

19. A process for preparation of a filtration device, the process comprising:

depositing the membrane comprising the water-channeling integral membrane proteins onto and/or into a porous support; and contacting the membrane comprising the water-channeling integral membrane proteins that is deposited onto and/or into the porous support with a silica precursor to form the silica layer on the first surface of the membrane.

20. The process according to claim 18, wherein the silica precursor is selected from the group consisting of a silicon alkoxide, a silane, a silicate, a silanol, a silazane, and any combination thereof.

* * * * *